(12) United States Patent
Tavernier et al.

(10) Patent No.: US 10,280,410 B2
(45) Date of Patent: *May 7, 2019

(54) CYTOPLASMIC PROTEIN COMPLEX COMPRISING A KINASE SUBSTRATE SENSOR CELLS AND ASSOCIATED DETECTION METHODS

(75) Inventors: Jan Tavernier, Balegem (BE); Samuel Lievens, Aalter (BE)

(73) Assignees: UNIVERSITEIT GENT, Gent (BE); VIB VZW, Gent (BE)

( * ) Notice: Subject to any disclaimer, the term of this patent is extended or adjusted under 35 U.S.C. 154(b) by 89 days.

This patent is subject to a terminal disclaimer.

(21) Appl. No.: 14/002,320

(22) PCT Filed: Feb. 29, 2012

(86) PCT No.: PCT/EP2012/053463
§ 371 (c)(1),
(2), (4) Date: Oct. 8, 2013

(87) PCT Pub. No.: WO2012/117031
PCT Pub. Date: Sep. 7, 2012

(65) Prior Publication Data
US 2014/0030746 A1    Jan. 30, 2014

Related U.S. Application Data

(60) Provisional application No. 61/464,285, filed on Mar. 1, 2011.

(30) Foreign Application Priority Data

Mar. 1, 2011  (GB) .................................... 1103453

(51) Int. Cl.
  *C12N 9/12*      (2006.01)
  *C12N 15/10*     (2006.01)
  *C12N 15/62*     (2006.01)
  *C12Q 1/48*      (2006.01)
  *G01N 33/542*    (2006.01)

(52) U.S. Cl.
  CPC ........... *C12N 9/12* (2013.01); *C12N 15/1055* (2013.01); *C12N 15/62* (2013.01); *C12Q 1/485* (2013.01); *G01N 33/542* (2013.01); *C07K 2319/00* (2013.01)

(58) Field of Classification Search
  CPC .................................................. C07K 2319/00
  See application file for complete search history.

(56) References Cited

U.S. PATENT DOCUMENTS

| | | | |
|---|---|---|---|
| 5,776,689 A | 7/1998 | Karin et al. | |
| 2002/0177217 A1* | 11/2002 | Krieger | C12N 15/1055 506/7 |
| 2003/0100021 A1 | 5/2003 | Eyckerman et al. | |
| 2005/0100934 A1 | 5/2005 | Lee et al. | |
| 2006/0147975 A1 | 7/2006 | Lee et al. | |
| 2010/0173408 A1 | 7/2010 | Eyckerman et al. | |
| 2012/0077706 A1 | 3/2012 | Lee et al. | |

FOREIGN PATENT DOCUMENTS

| | | |
|---|---|---|
| WO | 9002809 A1 | 3/1990 |
| WO | 9220790 A1 | 11/1992 |
| WO | 9710330 A1 | 3/1997 |
| WO | 9732017 A1 | 9/1997 |
| WO | 0190188 A2 | 11/2001 |
| WO | 2004062607 A2 | 7/2004 |
| WO | 2005007822 A2 | 1/2005 |
| WO | 2012117031 A1 | 9/2012 |

OTHER PUBLICATIONS

Eyckerman et al, Design and application of a cytokinereceptor-based interaction trap. Nat Cell Biol. Dec. 2001;3(12):1114-9.*
Lee et al, Casein kinase 2B as a novel enhancer of activin-like receptor-1 signaling. FASEB J. 23, 3712-3721 (2009).*
Staerk et al, JAK1 and Tyk2 activation by the homologous polycythemia vera JAK2 V617F mutation: cross-talk with IGF1 receptor. J Biol Chem. Dec. 23, 2005;280(51):41893-9. Epub Oct. 19, 2005.*
Urech et al, Cell growth selection system to detect extracellular and transmembrane protein interactions. Biochimica et Biophysica Acta 1622 (2003) 117-127.*
Oh et al, A receptor-independent, cell-based JAK activation assay for screening for JAK3-specific inhibitors. A receptor-independent, cell-based JAK activation assay for screening for JAK3-specific inhibitors.*
Constantinescu et al, Mining for JAK-STAT mutations in cancer. Trends in Biochemical Sciences 2008 vol. 33 No. 3 p. 122-131.*
Gauzzi et al, The amino-terminal region of Tyk2 sustains the level of interferon a receptor 1, a component of the interferon ayb receptor. Proc. Natl. Acad. Sci. USA vol. 94, pp. 11839-11844, Oct. 1997.*
Wang et al, Phosphorylation and Internalization of gp130 Occur After IL-6 Activation of Jak2 Kinase in Hepatocytes. Molecular Biology of the Cell vol. 5, 819-828, Jul. 1994.*
Hann et al, A single amino acid substitution (Trp(666)—>Ala) in the interbox1/2 region of the interleukin-6 signal transducer gp130 abrogates binding of JAK1, and dominantly impairs signal transduction. Biochem J. Jul. 1, 2000;349(Pt 1):261-6.*

(Continued)

*Primary Examiner* — Sheridan Swope
(74) *Attorney, Agent, or Firm* — Patent Law Works LLP

(57) ABSTRACT

The disclosure relates to a cytoplasmic protein complex comprising: (a) a first recombinant fusion protein comprising a kinase, fused to a first interaction polypeptide; and (b) a second recombinant fusion protein comprising a domain comprising a reporter phosphorylation site, whereby the domain is fused to a second interaction polypeptide. The disclosure relates further to a method to detect compound-compound-interaction using the cytoplasmic protein complex, and to cells comprising such cytoplasmic protein complex.

17 Claims, 4 Drawing Sheets
Specification includes a Sequence Listing.

(56) References Cited

OTHER PUBLICATIONS

Saharinen et al, The Pseudokinase Domain Is Required for Suppression of Basal Activity of Jak2 and Jak3 Tyrosine Kinases and for Cytokine-inducible Activation of Signal Transduction. J Biol Chem vol. 277, No. 49, pp. 47954-47963, 2002.*
Saharinen et al, Regulation of the Jak2 Tyrosine Kinase by Its Pseudokinase Domain. Mol & Cell Biology vol. 20, No. 10, 2000, p. 3387-3395.*
Shide et al, Tyk2 mutation homologous to V617F Jak2 is not found in essential thrombocythaemia, although it induces constitutive signaling and growth factor independence. Leukemia Research 31 (2007) 1077-1084.*
LabChip 3000 from Caliper LifeSciences downloaded Apr. 3, 2018.*
Korniski et al, Expression, purification, and characterization of TYK-2 kinase domain, a member of the Janus kinase family. Biochemical and Biophysical Research Communications 396 (2010) 543-548.*
Pattyn et al., MAPPIT (MAmmalian Protein-Protein Interaction Trap) as a tool to study HIV reverse transcriptase dimerization in intact human cells, Journal of Virological Methods, Oct. 1, 2008, pp. 7-15, vol. 153, No. 1, Elsevier BV, NL.
Lemmens et al., Strategies Towards High-Quality Binary Protein Interactome Maps, Journal of Proteomics, Jun. 16, 2010, pp. 1415-1420, vol. 73, No. 8, Elsevier, Amsterdam, NL.
Lievens et al., Mammalian two-hybrids come of age, Trends in Biochemical Sciences, Nov. 1, 2009, pp. 579-588, vol. 34, No. 11. Elsevier, Haywards, GB.
Suter et al., Two-hybrid Technologies in Proteomics Research, Current Opinion in Biotechnology, Aug. 1, 2008, pp. 316-323, vol. 19, No. 4, London, GB.
PCT International Search Report, PCT/EP2012/053463 dated Jun. 5, 2012.
Gonzalez-Nunez et al., The ALK-1/Smad1 pathway in cardiovascular physiopathology. A new target for therapy?, Biochimica et Biophysica Acta, 2013, pp. 1492-1510, vol. 1832.
Wellstein et al., Figure 1: The ALK receptor kinase: its domains, pathways, mutations and inhibitors, Nature Medicine, 2011, pp. 290-291, vol. 17, at http://www.nature.com/nm/journal/v17/n3/fig_tab/nm0311-290_F1.html (Apr. 28, 2016).
Lamouille, et al., Activin receptor-like kinase 1 is implicated in the maturation phase of angiogenesis, Hemostasis, Thrombosis, and Vascular Biology, Blood, Dec. 15, 2002, pp. 4495-4501, vol. 100.
Lievens et al., Kinase Substrate Sensor (KISS), a Mammalian In Situ Protein Interaction Sensor , 2014 Molecular and Cellular Proteomics, The American Society of Biochemistry and Molecular Biology Inc., pp. 3332-3342.

* cited by examiner

SEQUENCE LISTING

```
<160> NUMBER OF SEQ ID NOS: 27

<210> SEQ ID NO 1
<211> LENGTH: 599
<212> TYPE: PRT
<213> ORGANISM: Homo sapiens

<400> SEQUENCE: 1

Ile Thr Gln Leu Ser His Leu Gly Gln Gly Thr Arg Thr Asn Val Tyr
1               5                   10                  15

Glu Gly Arg Leu Arg Val Glu Gly Ser Gly Asp Pro Glu Glu Gly Lys
            20                  25                  30

Met Asp Asp Glu Asp Pro Leu Val Pro Gly Arg Asp Arg Gly Gln Glu
        35                  40                  45

Leu Arg Val Val Leu Lys Val Leu Asp Pro Ser His His Asp Ile Ala
    50                  55                  60

Leu Ala Phe Tyr Glu Thr Ala Ser Leu Met Ser Gln Val Ser His Thr
65                  70                  75                  80

His Leu Ala Phe Val His Gly Val Cys Val Arg Gly Pro Glu Asn Ile
                85                  90                  95

Met Val Thr Glu Tyr Val Glu His Gly Pro Leu Asp Val Trp Leu Arg
            100                 105                 110

Arg Glu Arg Gly His Val Pro Met Ala Trp Lys Met Val Val Ala Gln
        115                 120                 125

Gln Leu Ala Ser Ala Leu Ser Tyr Leu Glu Asn Lys Asn Leu Val His
    130                 135                 140

Gly Asn Val Cys Gly Arg Asn Ile Leu Leu Ala Arg Leu Gly Leu Ala
145                 150                 155                 160

Glu Gly Thr Ser Pro Phe Ile Lys Leu Ser Asp Pro Gly Val Gly Leu
                165                 170                 175
```

```
Gly Ala Leu Ser Arg Glu Arg Val Glu Arg Ile Pro Trp Leu Ala
            180                 185                 190

Pro Glu Cys Leu Pro Gly Ala Asn Ser Leu Ser Thr Ala Met Asp
            195                 200                 205

Lys Trp Gly Phe Gly Ala Thr Leu Leu Glu Ile Cys Phe Asp Gly Glu
            210                 215                 220

Ala Pro Leu Gln Ser Arg Ser Pro Ser Glu Lys Glu His Phe Tyr Gln
225                 230                 235                 240

Arg Gln His Arg Leu Pro Glu Pro Ser Cys Pro Gln Leu Ala Thr Leu
                245                 250                 255

Thr Ser Gln Cys Leu Thr Tyr Glu Pro Thr Gln Arg Pro Ser Phe Arg
            260                 265                 270

Thr Ile Leu Arg Asp Leu Thr Arg Leu Gln Pro His Asn Leu Ala Asp
            275                 280                 285

Val Leu Thr Val Asn Pro Asp Ser Pro Ala Ser Asp Pro Thr Val Phe
            290                 295                 300

His Lys Arg Tyr Leu Lys Lys Ile Arg Asp Leu Gly Glu Gly His Phe
305                 310                 315                 320

Gly Lys Val Ser Leu Tyr Cys Tyr Asp Pro Thr Asn Asp Gly Thr Gly
                325                 330                 335

Glu Met Val Ala Val Lys Ala Leu Lys Ala Asp Cys Gly Pro Gln His
            340                 345                 350

Arg Ser Gly Trp Lys Gln Glu Ile Asp Ile Leu Arg Thr Leu Tyr His
            355                 360                 365

Glu His Ile Ile Lys Tyr Lys Gly Cys Cys Glu Asp Gln Gly Glu Lys
            370                 375                 380

Ser Leu Gln Leu Val Met Glu Tyr Val Pro Leu Gly Ser Leu Arg Asp
385                 390                 395                 400

Tyr Leu Pro Arg His Ser Ile Gly Leu Ala Gln Leu Leu Leu Phe Ala
                405                 410                 415

Gln Gln Ile Cys Glu Gly Met Ala Tyr Leu His Ala Gln His Tyr Ile
            420                 425                 430

His Arg Asp Leu Ala Ala Arg Asn Val Leu Leu Asp Asn Asp Arg Leu
            435                 440                 445

Val Lys Ile Gly Asp Phe Gly Leu Ala Lys Ala Val Pro Glu Gly His
            450                 455                 460

Glu Tyr Tyr Arg Val Arg Glu Asp Gly Asp Ser Pro Val Phe Trp Tyr
465                 470                 475                 480

Ala Pro Glu Cys Leu Lys Glu Tyr Lys Phe Tyr Tyr Ala Ser Asp Val
                485                 490                 495

Trp Ser Phe Gly Val Thr Leu Tyr Glu Leu Leu Thr His Cys Asp Ser
            500                 505                 510

Ser Gln Ser Pro Pro Thr Lys Phe Leu Glu Leu Ile Gly Ile Ala Gln
            515                 520                 525

Gly Gln Met Thr Val Leu Arg Leu Thr Glu Leu Leu Glu Arg Gly Glu
            530                 535                 540

Arg Leu Pro Arg Pro Asp Lys Cys Pro Cys Glu Val Tyr His Leu Met
545                 550                 555                 560

Lys Asn Cys Trp Glu Thr Glu Ala Ser Phe Arg Pro Thr Phe Glu Asn
                565                 570                 575

Leu Ile Pro Ile Leu Lys Thr Val His Glu Lys Tyr Gln Gly Gln Ala
            580                 585                 590
```

```
Pro Ser Val Phe Ser Val Cys
        595

<210> SEQ ID NO 2
<211> LENGTH: 304
<212> TYPE: PRT
<213> ORGANISM: Homo sapiens

<400> SEQUENCE: 2

Ser Pro Ala Ser Asp Pro Thr Val Phe His Lys Arg Tyr Leu Lys Lys
1               5                   10                  15

Ile Arg Asp Leu Gly Glu Gly His Phe Gly Lys Val Ser Leu Tyr Cys
            20                  25                  30

Tyr Asp Pro Thr Asn Asp Gly Thr Gly Glu Met Val Ala Val Lys Ala
        35                  40                  45

Leu Lys Ala Asp Cys Gly Pro Gln His Arg Ser Gly Trp Lys Gln Glu
    50                  55                  60

Ile Asp Ile Leu Arg Thr Leu Tyr His Glu His Ile Ile Lys Tyr Lys
65                  70                  75                  80

Gly Cys Cys Glu Asp Gln Gly Glu Lys Ser Leu Gln Leu Val Met Glu
                85                  90                  95

Tyr Val Pro Leu Gly Ser Leu Arg Asp Tyr Leu Pro Arg His Ser Ile
            100                 105                 110

Gly Leu Ala Gln Leu Leu Leu Phe Ala Gln Gln Ile Cys Glu Gly Met
        115                 120                 125

Ala Tyr Leu His Ala Gln His Tyr Ile His Arg Asp Leu Ala Ala Arg
    130                 135                 140

Asn Val Leu Leu Asp Asn Asp Arg Leu Val Lys Ile Gly Asp Phe Gly
145                 150                 155                 160

Leu Ala Lys Ala Val Pro Glu Gly His Glu Tyr Tyr Arg Val Arg Glu
                165                 170                 175

Asp Gly Asp Ser Pro Val Phe Trp Tyr Ala Pro Glu Cys Leu Lys Glu
            180                 185                 190

Tyr Lys Phe Tyr Tyr Ala Ser Asp Val Trp Ser Phe Gly Val Thr Leu
        195                 200                 205

Tyr Glu Leu Leu Thr His Cys Asp Ser Ser Gln Ser Pro Pro Thr Lys
    210                 215                 220

Phe Leu Glu Leu Ile Gly Ile Ala Gln Gly Gln Met Thr Val Leu Arg
225                 230                 235                 240

Leu Thr Glu Leu Leu Glu Arg Gly Glu Arg Leu Pro Arg Pro Asp Lys
                245                 250                 255

Cys Pro Cys Glu Val Tyr His Leu Met Lys Asn Cys Trp Glu Thr Glu
            260                 265                 270

Ala Ser Phe Arg Pro Thr Phe Glu Asn Leu Ile Pro Ile Leu Lys Thr
        275                 280                 285

Val His Glu Lys Tyr Gln Gly Gln Ala Pro Ser Val Phe Ser Val Cys
    290                 295                 300

<210> SEQ ID NO 3
<211> LENGTH: 159
<212> TYPE: PRT
<213> ORGANISM: Homo sapiens

<400> SEQUENCE: 3

Ser Thr Val Val His Ser Gly Tyr Arg His Gln Val Pro Ser Val Gln
1               5                   10                  15
```

Val Phe Ser Arg Ser Glu Ser Thr Gln Pro Leu Leu Asp Ser Glu Glu
            20                  25                  30

Arg Pro Glu Asp Leu Gln Leu Val Asp His Val Asp Gly Gly Asp Gly
            35                  40                  45

Ile Leu Pro Arg Gln Gln Tyr Phe Lys Gln Asn Cys Ser Gln His Glu
50                      55                  60

Ser Ser Pro Asp Ile Ser His Phe Glu Arg Ser Lys Gln Val Ser Ser
65                  70                  75                  80

Val Asn Glu Glu Asp Phe Val Arg Leu Lys Gln Gln Ile Ser Asp His
                85                  90                  95

Ile Ser Gln Ser Cys Gly Ser Gly Gln Met Lys Met Phe Gln Glu Val
            100                 105                 110

Ser Ala Ala Asp Ala Phe Gly Pro Gly Thr Glu Gly Gln Val Glu Arg
            115                 120                 125

Phe Glu Thr Val Gly Met Glu Ala Ala Thr Asp Glu Gly Met Pro Lys
            130                 135                 140

Ser Tyr Leu Pro Gln Thr Val Arg Gln Gly Gly Tyr Met Pro Gln
145                 150                 155

<210> SEQ ID NO 4
<211> LENGTH: 187
<212> TYPE: PRT
<213> ORGANISM: Homo sapiens

<400> SEQUENCE: 4

Ser Thr Val Val His Ser Gly Tyr Arg His Gln Val Pro Ser Val Gln
1               5                   10                  15

Val Phe Ser Arg Ser Glu Ser Thr Gln Pro Leu Leu Asp Ser Glu Glu
            20                  25                  30

Arg Pro Glu Asp Leu Gln Leu Val Asp His Val Asp Gly Gly Asp Gly
            35                  40                  45

Ile Leu Pro Arg Gln Gln Tyr Phe Lys Gln Asn Cys Ser Gln His Glu
50                      55                  60

Ser Ser Pro Asp Ile Ser His Phe Glu Arg Ser Lys Gln Val Ser Ser
65                  70                  75                  80

Val Asn Glu Glu Asp Phe Val Arg Leu Lys Gln Gln Ile Ser Asp His
                85                  90                  95

Ile Ser Gln Ser Cys Gly Ser Gly Gln Met Lys Met Phe Gln Glu Val
            100                 105                 110

Ser Ala Ala Asp Ala Phe Gly Pro Gly Thr Glu Gly Gln Val Glu Arg
            115                 120                 125

Phe Glu Thr Val Gly Met Glu Ala Ala Thr Asp Glu Gly Met Pro Lys
            130                 135                 140

Ser Tyr Leu Pro Gln Thr Val Arg Gln Gly Gly Tyr Met Pro Gln Gly
145                 150                 155                 160

Gly Ser Glu Leu Ser Thr Ser Leu Tyr Lys Lys Ala Gly Tyr Leu Pro
                165                 170                 175

Gln Thr Val Arg Gln Gly Gly Tyr Met Pro Gln
            180                 185

<210> SEQ ID NO 5
<211> LENGTH: 598
<212> TYPE: PRT
<213> ORGANISM: Mus musculus

<400> SEQUENCE: 5

```
Met Val Phe His Lys Ile Arg Asn Glu Asp Leu Ile Phe Asn Glu Ser
1               5                   10                  15
Leu Gly Gln Gly Thr Phe Thr Lys Ile Phe Lys Gly Val Arg Arg Glu
            20                  25                  30
Val Gly Asp Tyr Gly Gln Leu His Lys Thr Glu Val Leu Leu Lys Val
        35                  40                  45
Leu Asp Lys Ala His Arg Asn Tyr Ser Glu Ser Phe Phe Glu Ala Ala
    50                  55                  60
Ser Met Met Ser Gln Leu Ser His Lys His Leu Val Leu Asn Tyr Gly
65                  70                  75                  80
Val Cys Val Cys Gly Glu Glu Asn Ile Leu Val Gln Glu Phe Val Lys
            85                  90                  95
Phe Gly Ser Leu Asp Thr Tyr Leu Lys Lys Asn Lys Asn Ser Ile Asn
            100                 105                 110
Ile Leu Trp Lys Leu Gly Val Ala Lys Gln Leu Ala Trp Ala Met His
            115                 120                 125
Phe Leu Glu Glu Lys Ser Leu Ile His Gly Asn Val Cys Ala Lys Asn
    130                 135                 140
Ile Leu Leu Ile Arg Glu Glu Asp Arg Arg Thr Gly Asn Pro Pro Phe
145                 150                 155                 160
Ile Lys Leu Ser Asp Pro Gly Ile Ser Ile Thr Val Leu Pro Lys Asp
            165                 170                 175
Ile Leu Gln Glu Arg Ile Pro Trp Val Pro Pro Glu Cys Ile Glu Asn
            180                 185                 190
Pro Lys Asn Leu Asn Leu Ala Thr Asp Lys Trp Ser Phe Gly Thr Thr
    195                 200                 205
Leu Trp Glu Ile Cys Ser Gly Gly Asp Lys Pro Leu Ser Ala Leu Asp
    210                 215                 220
Ser Gln Arg Lys Leu Gln Phe Tyr Glu Asp Lys His Gln Leu Pro Ala
225                 230                 235                 240
Pro Lys Trp Thr Glu Leu Ala Asn Leu Ile Asn Asn Cys Met Asp Tyr
            245                 250                 255
Glu Pro Asp Phe Arg Pro Ala Phe Arg Ala Val Ile Arg Asp Leu Asn
            260                 265                 270
Ser Leu Phe Thr Pro Asp Tyr Glu Leu Leu Thr Glu Asn Asp Met Leu
            275                 280                 285
Pro Asn Met Arg Ile Gly Ala Leu Gly Phe Ser Gly Ala Phe Glu Asp
    290                 295                 300
Arg Asp Pro Thr Gln Phe Glu Glu Arg His Leu Lys Phe Leu Gln Gln
305                 310                 315                 320
Leu Gly Lys Gly Asn Phe Gly Ser Val Glu Met Cys Arg Tyr Asp Pro
            325                 330                 335
Leu Gln Asp Asn Thr Gly Glu Val Val Ala Val Lys Lys Leu Gln His
            340                 345                 350
Ser Thr Glu Glu His Leu Arg Asp Phe Glu Arg Glu Ile Glu Ile Leu
            355                 360                 365
Lys Ser Leu Gln His Asp Asn Ile Val Lys Tyr Lys Gly Val Cys Tyr
    370                 375                 380
Ser Ala Gly Arg Arg Asn Leu Arg Leu Ile Met Glu Tyr Leu Pro Tyr
385                 390                 395                 400
Gly Ser Leu Arg Asp Tyr Leu Gln Lys His Lys Glu Arg Ile Asp His
            405                 410                 415
Lys Lys Leu Leu Gln Tyr Thr Ser Gln Ile Cys Lys Gly Met Glu Tyr
```

```
            420                 425                 430
Leu Gly Thr Lys Arg Tyr Ile His Arg Asp Leu Ala Thr Arg Asn Ile
        435                 440                 445

Leu Val Glu Asn Glu Asn Arg Val Lys Ile Gly Asp Phe Gly Leu Thr
    450                 455                 460

Lys Val Leu Pro Gln Asp Lys Glu Tyr Tyr Lys Val Lys Glu Pro Gly
465                 470                 475                 480

Glu Ser Pro Ile Phe Trp Tyr Ala Pro Glu Ser Leu Thr Glu Ser Lys
                485                 490                 495

Phe Ser Val Ala Ser Asp Val Trp Ser Phe Gly Val Val Leu Tyr Glu
            500                 505                 510

Leu Phe Thr Tyr Ile Glu Lys Ser Lys Ser Pro Pro Val Glu Phe Met
        515                 520                 525

Arg Met Ile Gly Asn Asp Lys Gln Gly Gln Met Ile Val Phe His Leu
    530                 535                 540

Ile Glu Leu Leu Lys Ser Asn Gly Arg Leu Pro Arg Pro Glu Gly Cys
545                 550                 555                 560

Pro Asp Glu Ile Tyr Val Ile Met Thr Glu Cys Trp Asn Asn Asn Val
                565                 570                 575

Ser Gln Arg Pro Ser Phe Arg Asp Leu Ser Leu Arg Val Asp Gln Ile
            580                 585                 590

Arg Asp Ser Ile Ala Ala
        595

<210> SEQ ID NO 6
<211> LENGTH: 308
<212> TYPE: PRT
<213> ORGANISM: Mus musculus

<400> SEQUENCE: 6

Met Arg Ile Gly Ala Leu Gly Phe Ser Gly Ala Phe Glu Asp Arg Asp
1               5                   10                  15

Pro Thr Gln Phe Glu Glu Arg His Leu Lys Phe Leu Gln Gln Leu Gly
            20                  25                  30

Lys Gly Asn Phe Gly Ser Val Glu Met Cys Arg Tyr Asp Pro Leu Gln
        35                  40                  45

Asp Asn Thr Gly Glu Val Val Ala Val Lys Lys Leu Gln His Ser Thr
    50                  55                  60

Glu Glu His Leu Arg Asp Phe Glu Arg Glu Ile Glu Ile Leu Lys Ser
65                  70                  75                  80

Leu Gln His Asp Asn Ile Val Lys Tyr Lys Gly Val Cys Tyr Ser Ala
                85                  90                  95

Gly Arg Arg Asn Leu Arg Leu Ile Met Glu Tyr Leu Pro Tyr Gly Ser
            100                 105                 110

Leu Arg Asp Tyr Leu Gln Lys His Lys Glu Arg Ile Asp His Lys Lys
        115                 120                 125

Leu Leu Gln Tyr Thr Ser Gln Ile Cys Lys Gly Met Glu Tyr Leu Gly
    130                 135                 140

Thr Lys Arg Tyr Ile His Arg Asp Leu Ala Thr Arg Asn Ile Leu Val
145                 150                 155                 160

Glu Asn Glu Asn Arg Val Lys Ile Gly Asp Phe Gly Leu Thr Lys Val
                165                 170                 175

Leu Pro Gln Asp Lys Glu Tyr Tyr Lys Val Lys Glu Pro Gly Glu Ser
            180                 185                 190
```

```
Pro Ile Phe Trp Tyr Ala Pro Glu Ser Leu Thr Glu Ser Lys Phe Ser
        195                 200                 205

Val Ala Ser Asp Val Trp Ser Phe Gly Val Val Leu Tyr Glu Leu Phe
    210                 215                 220

Thr Tyr Ile Glu Lys Ser Lys Ser Pro Pro Val Glu Phe Met Arg Met
225                 230                 235                 240

Ile Gly Asn Asp Lys Gln Gly Gln Met Ile Val Phe His Leu Ile Glu
                245                 250                 255

Leu Leu Lys Ser Asn Gly Arg Leu Pro Arg Pro Glu Gly Cys Pro Asp
            260                 265                 270

Glu Ile Tyr Val Ile Met Thr Glu Cys Trp Asn Asn Asn Val Ser Gln
        275                 280                 285

Arg Pro Ser Phe Arg Asp Leu Ser Leu Arg Val Asp Gln Ile Arg Asp
    290                 295                 300

Ser Ile Ala Ala
305

<210> SEQ ID NO 7
<211> LENGTH: 258
<212> TYPE: PRT
<213> ORGANISM: Homo sapiens

<400> SEQUENCE: 7

Pro Arg Glu Ser Leu Arg Leu Glu Val Lys Leu Gly Gln Gly Cys Phe
1               5                   10                  15

Gly Glu Val Trp Met Gly Thr Trp Asn Gly Thr Thr Arg Val Ala Ile
            20                  25                  30

Lys Thr Leu Lys Pro Gly Thr Met Ser Pro Glu Ala Phe Leu Gln Glu
        35                  40                  45

Ala Gln Val Met Lys Lys Leu Arg His Glu Lys Leu Val Gln Leu Tyr
    50                  55                  60

Ala Val Val Ser Glu Glu Pro Ile Tyr Ile Val Thr Glu Tyr Met Ser
65                  70                  75                  80

Lys Gly Ser Leu Leu Asp Phe Leu Lys Gly Glu Thr Gly Lys Tyr Leu
                85                  90                  95

Arg Leu Pro Gln Leu Val Asp Met Ala Ala Gln Ile Ala Ser Gly Met
            100                 105                 110

Ala Tyr Val Glu Arg Met Asn Tyr Val His Arg Asp Leu Arg Ala Ala
        115                 120                 125

Asn Ile Leu Val Gly Glu Asn Leu Val Cys Lys Val Ala Asp Phe Gly
    130                 135                 140

Leu Ala Arg Leu Ile Glu Asp Asn Glu Tyr Thr Ala Arg Gln Gly Ala
145                 150                 155                 160

Lys Phe Pro Ile Lys Trp Thr Ala Pro Glu Ala Ala Leu Tyr Gly Arg
                165                 170                 175

Phe Thr Ile Lys Ser Asp Val Trp Ser Phe Gly Ile Leu Leu Thr Glu
            180                 185                 190

Leu Thr Thr Lys Gly Arg Val Pro Tyr Pro Gly Met Val Asn Arg Glu
        195                 200                 205

Val Leu Asp Gln Val Glu Arg Gly Tyr Arg Met Pro Cys Pro Pro Glu
    210                 215                 220

Cys Pro Glu Ser Leu His Asp Leu Met Cys Gln Cys Trp Arg Lys Glu
225                 230                 235                 240

Pro Glu Glu Arg Pro Thr Phe Glu Tyr Leu Gln Ala Phe Leu Glu Asp
                245                 250                 255
```

Tyr Phe

<210> SEQ ID NO 8
<211> LENGTH: 73
<212> TYPE: DNA
<213> ORGANISM: Artificial Sequence
<220> FEATURE:
<223> OTHER INFORMATION: Primer

<400> SEQUENCE: 8
cccgggccca ccatgtatcc atatgatgtt ccagattatg ctttaattaa aatcacccag    60
ctgtcccact tgg                                                       73

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
ggggaattcg cacacgctga acactgaagg                                     30

<210> SEQ ID NO 10
<211> LENGTH: 45
<212> TYPE: DNA
<213> ORGANISM: Artificial Sequence
<220> FEATURE:
<223> OTHER INFORMATION: Primer

<400> SEQUENCE: 10
cgtacgaatt cgggagctcg atgactcgcg atttcaaacc tggag                    45

<210> SEQ ID NO 11
<211> LENGTH: 48
<212> TYPE: DNA
<213> ORGANISM: Artificial Sequence
<220> FEATURE:
<223> OTHER INFORMATION: Primer

<400> SEQUENCE: 11
ggtcatctag accgcggccg ctcagttatc tagtgtagaa tccttcag                 48

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
gcggaattca tgtgcaatac caacatgtct g                                   31

<210> SEQ ID NO 13
<211> LENGTH: 32
<212> TYPE: DNA
<213> ORGANISM: Artificial Sequence
<220> FEATURE:
<223> OTHER INFORMATION: Primer

<400> SEQUENCE: 13
cgcgcggccg cctaggggaa ataagttagc ac                                  32

<210> SEQ ID NO 14

-continued

```
<211> LENGTH: 30
<212> TYPE: DNA
<213> ORGANISM: Artificial Sequence
<220> FEATURE:
<223> OTHER INFORMATION: Primer

<400> SEQUENCE: 14
gcgagaattc gaggagccgc agtcagatcc                                    30

<210> SEQ ID NO 15
<211> LENGTH: 34
<212> TYPE: DNA
<213> ORGANISM: Artificial Sequence
<220> FEATURE:
<223> OTHER INFORMATION: Primer

<400> SEQUENCE: 15
cgctgcggcc gcttagcggg gagcagcctc tggc                               34

<210> SEQ ID NO 16
<211> LENGTH: 41
<212> TYPE: DNA
<213> ORGANISM: Artificial Sequence
<220> FEATURE:
<223> OTHER INFORMATION: Primer

<400> SEQUENCE: 16
cccgcggccg ctttaattaa aatggtgttt cacaaaatca g                       41

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17
gggctcgagg aattccgcag ctatactgtc ccgg                               34

<210> SEQ ID NO 18
<211> LENGTH: 40
<212> TYPE: DNA
<213> ORGANISM: Artificial Sequence
<220> FEATURE:
<223> OTHER INFORMATION: Primer

<400> SEQUENCE: 18
cccgcggccg ctttaattaa acctcgggag tcgctgcggc                         40

<210> SEQ ID NO 19
<211> LENGTH: 35
<212> TYPE: DNA
<213> ORGANISM: Artificial Sequence
<220> FEATURE:
<223> OTHER INFORMATION: Primer

<400> SEQUENCE: 19
gggctcgagg aattcgaagt agtcctccag gaagg                              35

<210> SEQ ID NO 20
<211> LENGTH: 36
<212> TYPE: DNA
<213> ORGANISM: Artificial Sequence
<220> FEATURE:
<223> OTHER INFORMATION: Primer

<400> SEQUENCE: 20
```
cgtacgaatt cgggagctcg tttttagatg gaatag       36

<210> SEQ ID NO 21
<211> LENGTH: 41
<212> TYPE: DNA
<213> ORGANISM: Artificial Sequence
<220> FEATURE:
<223> OTHER INFORMATION: Primer

<400> SEQUENCE: 21
ggtcatctag accgcggccg ctcaatcctc atcctgtcta c       41

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
catttaatta aacctctgcg ccactggggg       30

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
catgaattcg cacacgctga acactgaagg g       31

<210> SEQ ID NO 24
<211> LENGTH: 29
<212> TYPE: DNA
<213> ORGANISM: Artificial Sequence
<220> FEATURE:
<223> OTHER INFORMATION: Primer

<400> SEQUENCE: 24
ccgagaccta gccgcggcca acgtgctgc       29

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
gcagcacgtt ggccgcggct aggtctcgg       29

<210> SEQ ID NO 26
<211> LENGTH: 1187
<212> TYPE: PRT
<213> ORGANISM: Homo sapiens

<400> SEQUENCE: 26

Met Pro Leu Arg His Trp Gly Met Ala Arg Gly Ser Lys Pro Val Gly
1               5                   10                  15

Asp Gly Ala Gln Pro Met Ala Ala Met Gly Gly Leu Lys Val Leu Leu
            20                  25                  30

His Trp Ala Gly Pro Gly Gly Gly Glu Pro Trp Val Thr Phe Ser Glu
        35                  40                  45

```
Ser Ser Leu Thr Ala Glu Glu Val Cys Ile His Ile Ala His Lys Val
 50                  55                  60

Gly Ile Thr Pro Pro Cys Phe Asn Leu Phe Ala Leu Phe Asp Ala Gln
 65                  70                  75                  80

Ala Gln Val Trp Leu Pro Pro Asn His Ile Leu Glu Ile Pro Arg Asp
                 85                  90                  95

Ala Ser Leu Met Leu Tyr Phe Arg Ile Arg Phe Tyr Phe Arg Asn Trp
            100                 105                 110

His Gly Met Asn Pro Arg Glu Pro Ala Val Tyr Arg Cys Gly Pro Pro
        115                 120                 125

Gly Thr Glu Ala Ser Ser Asp Gln Thr Ala Gln Gly Met Gln Leu Leu
    130                 135                 140

Asp Pro Ala Ser Phe Glu Tyr Leu Phe Glu Gln Gly Lys His Glu Phe
145                 150                 155                 160

Val Asn Asp Val Ala Ser Leu Trp Glu Leu Ser Thr Glu Glu Glu Ile
                165                 170                 175

His His Phe Lys Asn Glu Ser Leu Gly Met Ala Phe Leu His Leu Cys
            180                 185                 190

His Leu Ala Leu Arg His Gly Ile Pro Leu Glu Glu Val Ala Lys Lys
        195                 200                 205

Thr Ser Phe Lys Asp Cys Ile Pro Arg Ser Phe Arg Arg His Ile Arg
    210                 215                 220

Gln His Ser Ala Leu Thr Arg Leu Arg Leu Arg Asn Val Phe Arg Arg
225                 230                 235                 240

Phe Leu Arg Asp Phe Gln Pro Gly Arg Leu Ser Gln Gln Met Val Met
                245                 250                 255

Val Lys Tyr Leu Ala Thr Leu Glu Arg Leu Ala Pro Arg Phe Gly Thr
            260                 265                 270

Glu Arg Val Pro Val Cys His Leu Arg Leu Leu Ala Gln Ala Glu Gly
        275                 280                 285

Glu Pro Cys Tyr Ile Arg Asp Ser Gly Val Ala Pro Thr Asp Pro Gly
    290                 295                 300

Pro Glu Ser Ala Ala Gly Pro Pro Thr His Glu Val Leu Val Thr Gly
305                 310                 315                 320

Thr Gly Gly Ile Gln Trp Trp Pro Val Glu Glu Glu Val Asn Lys Glu
                325                 330                 335

Glu Gly Ser Ser Gly Ser Ser Gly Arg Asn Pro Gln Ala Ser Leu Phe
            340                 345                 350

Gly Lys Lys Ala Lys Ala His Lys Ala Val Gly Gln Pro Ala Asp Arg
        355                 360                 365

Pro Arg Glu Pro Leu Trp Ala Tyr Phe Cys Asp Phe Arg Asp Ile Thr
    370                 375                 380

His Val Val Leu Lys Glu His Cys Val Ser Ile His Arg Gln Asp Asn
385                 390                 395                 400

Lys Cys Leu Glu Leu Ser Leu Pro Ser Arg Ala Ala Leu Ser Phe
                405                 410                 415

Val Ser Leu Val Asp Gly Tyr Phe Arg Leu Thr Ala Asp Ser Ser His
            420                 425                 430

Tyr Leu Cys His Glu Val Ala Pro Pro Arg Leu Val Met Ser Ile Arg
        435                 440                 445

Asp Gly Ile His Gly Pro Leu Leu Glu Pro Phe Val Gln Ala Lys Leu
    450                 455                 460
```

```
Arg Pro Glu Asp Gly Leu Tyr Leu Ile His Trp Ser Thr Ser His Pro
465                 470                 475                 480

Tyr Arg Leu Ile Leu Thr Val Ala Gln Arg Ser Gln Ala Pro Asp Gly
            485                 490                 495

Met Gln Ser Leu Arg Leu Arg Lys Phe Pro Ile Glu Gln Gln Asp Gly
        500                 505                 510

Ala Phe Val Leu Glu Gly Trp Gly Arg Ser Phe Pro Ser Val Arg Glu
    515                 520                 525

Leu Gly Ala Ala Leu Gln Gly Cys Leu Leu Arg Ala Gly Asp Asp Cys
530                 535                 540

Phe Ser Leu Arg Arg Cys Cys Leu Pro Gln Pro Gly Glu Thr Ser Asn
545                 550                 555                 560

Leu Ile Ile Met Arg Gly Ala Arg Ala Ser Pro Arg Thr Leu Asn Leu
                565                 570                 575

Ser Gln Leu Ser Phe His Arg Val Asp Gln Lys Glu Ile Thr Gln Leu
            580                 585                 590

Ser His Leu Gly Gln Gly Thr Arg Thr Asn Val Tyr Glu Gly Arg Leu
        595                 600                 605

Arg Val Glu Gly Ser Gly Asp Pro Glu Glu Gly Lys Met Asp Asp Glu
610                 615                 620

Asp Pro Leu Val Pro Gly Arg Asp Arg Gly Gln Glu Leu Arg Val Val
625                 630                 635                 640

Leu Lys Val Leu Asp Pro Ser His His Asp Ile Ala Leu Ala Phe Tyr
                645                 650                 655

Glu Thr Ala Ser Leu Met Ser Gln Val Ser His Thr His Leu Ala Phe
            660                 665                 670

Val His Gly Val Cys Val Arg Gly Pro Glu Asn Ile Met Val Thr Glu
        675                 680                 685

Tyr Val Glu His Gly Pro Leu Asp Val Trp Leu Arg Arg Glu Arg Gly
690                 695                 700

His Val Pro Met Ala Trp Lys Met Val Val Ala Gln Gln Leu Ala Ser
705                 710                 715                 720

Ala Leu Ser Tyr Leu Glu Asn Lys Asn Leu Val His Gly Asn Val Cys
                725                 730                 735

Gly Arg Asn Ile Leu Leu Ala Arg Leu Gly Leu Ala Glu Gly Thr Ser
            740                 745                 750

Pro Phe Ile Lys Leu Ser Asp Pro Gly Val Gly Leu Gly Ala Leu Ser
        755                 760                 765

Arg Glu Glu Arg Val Glu Arg Ile Pro Trp Leu Ala Pro Glu Cys Leu
770                 775                 780

Pro Gly Gly Ala Asn Ser Leu Ser Thr Ala Met Asp Lys Trp Gly Phe
785                 790                 795                 800

Gly Ala Thr Leu Leu Glu Ile Cys Phe Asp Gly Glu Ala Pro Leu Gln
                805                 810                 815

Ser Arg Ser Pro Ser Glu Lys Glu His Phe Tyr Gln Arg Gln His Arg
            820                 825                 830

Leu Pro Glu Pro Ser Cys Pro Gln Leu Ala Thr Leu Thr Ser Gln Cys
        835                 840                 845

Leu Thr Tyr Glu Pro Thr Gln Arg Pro Ser Phe Arg Thr Ile Leu Arg
850                 855                 860

Asp Leu Thr Arg Leu Gln Pro His Asn Leu Ala Asp Val Leu Thr Val
865                 870                 875                 880

Asn Pro Asp Ser Pro Ala Ser Asp Pro Thr Val Phe His Lys Arg Tyr
```

```
                        885                 890                 895
Leu Lys Lys Ile Arg Asp Leu Gly Glu Gly His Phe Gly Lys Val Ser
                900                 905                 910

Leu Tyr Cys Tyr Asp Pro Thr Asn Asp Gly Thr Gly Glu Met Val Ala
            915                 920                 925

Val Lys Ala Leu Lys Ala Asp Cys Gly Pro Gln His Arg Ser Gly Trp
        930                 935                 940

Lys Gln Glu Ile Asp Ile Leu Arg Thr Leu Tyr His Glu His Ile Ile
945                 950                 955                 960

Lys Tyr Lys Gly Cys Cys Glu Asp Gln Gly Glu Lys Ser Leu Gln Leu
                965                 970                 975

Val Met Glu Tyr Val Pro Leu Gly Ser Leu Arg Asp Tyr Leu Pro Arg
            980                 985                 990

His Ser Ile Gly Leu Ala Gln Leu Leu Leu Phe Ala Gln Gln Ile Cys
        995                 1000                1005

Glu Gly Met Ala Tyr Leu His Ala Gln His Tyr Ile His Arg Asp
    1010                1015                1020

Leu Ala Ala Arg Asn Val Leu Leu Asp Asn Asp Arg Leu Val Lys
    1025                1030                1035

Ile Gly Asp Phe Gly Leu Ala Lys Ala Val Pro Glu Gly His Glu
    1040                1045                1050

Tyr Tyr Arg Val Arg Glu Asp Gly Asp Ser Pro Val Phe Trp Tyr
    1055                1060                1065

Ala Pro Glu Cys Leu Lys Glu Tyr Lys Phe Tyr Tyr Ala Ser Asp
    1070                1075                1080

Val Trp Ser Phe Gly Val Thr Leu Tyr Glu Leu Leu Thr His Cys
    1085                1090                1095

Asp Ser Ser Gln Ser Pro Pro Thr Lys Phe Leu Glu Leu Ile Gly
    1100                1105                1110

Ile Ala Gln Gly Gln Met Thr Val Leu Arg Leu Thr Glu Leu Leu
    1115                1120                1125

Glu Arg Gly Glu Arg Leu Pro Arg Pro Asp Lys Cys Pro Cys Glu
    1130                1135                1140

Val Tyr His Leu Met Lys Asn Cys Trp Glu Thr Glu Ala Ser Phe
    1145                1150                1155

Arg Pro Thr Phe Glu Asn Leu Ile Pro Ile Leu Lys Thr Val His
    1160                1165                1170

Glu Lys Tyr Gln Gly Gln Ala Pro Ser Val Phe Ser Val Cys
    1175                1180                1185

<210> SEQ ID NO 27
<211> LENGTH: 522
<212> TYPE: PRT
<213> ORGANISM: Homo sapiens

<400> SEQUENCE: 27

Gly Ser Asn Lys Ser Lys Pro Lys Asp Ala Ser Gln Arg Arg Arg Ser
1               5                   10                  15

Leu Glu Pro Ala Glu Asn Val His Gly Ala Gly Gly Gly Ala Phe Pro
            20                  25                  30

Ala Ser Gln Thr Pro Ser Lys Pro Ala Ser Ala Asp Gly His Arg Gly
        35                  40                  45

Pro Ser Ala Ala Phe Ala Pro Ala Ala Ala Glu Pro Lys Leu Phe Gly
    50                  55                  60
```

```
Gly Phe Asn Ser Ser Asp Thr Val Thr Ser Pro Gln Arg Ala Gly Pro
 65                  70                  75                  80

Leu Ala Gly Gly Val Thr Thr Phe Val Ala Leu Tyr Asp Tyr Glu Ser
                 85                  90                  95

Arg Thr Glu Thr Asp Leu Ser Phe Lys Lys Gly Glu Arg Leu Gln Ile
            100                 105                 110

Val Asn Asn Thr Glu Gly Asp Trp Trp Leu Ala His Ser Leu Ser Thr
        115                 120                 125

Gly Gln Thr Gly Tyr Ile Pro Ser Asn Tyr Val Ala Pro Ser Asp Ser
    130                 135                 140

Ile Gln Ala Glu Glu Trp Tyr Phe Gly Lys Ile Thr Arg Arg Glu Ser
145                 150                 155                 160

Glu Arg Leu Leu Leu Asn Ala Glu Asn Pro Arg Gly Thr Phe Leu Val
                165                 170                 175

Arg Glu Ser Glu Thr Thr Lys Gly Ala Tyr Cys Leu Ser Val Ser Asp
            180                 185                 190

Phe Asp Asn Ala Lys Gly Leu Asn Val Lys His Tyr Lys Ile Arg Lys
        195                 200                 205

Leu Asp Ser Gly Gly Phe Tyr Ile Thr Ser Arg Thr Gln Phe Asn Ser
    210                 215                 220

Leu Gln Gln Leu Val Ala Tyr Tyr Ser Lys His Ala Asp Gly Leu Cys
225                 230                 235                 240

His Arg Leu Thr Thr Val Cys Pro Thr Ser Lys Pro Gln Thr Gln Gly
                245                 250                 255

Leu Ala Lys Asp Ala Trp Glu Ile Pro Arg Glu Ser Leu Arg Leu Glu
            260                 265                 270

Val Lys Leu Gly Gln Gly Cys Phe Gly Glu Val Trp Met Gly Thr Trp
        275                 280                 285

Asn Gly Thr Thr Arg Val Ala Ile Lys Thr Leu Lys Pro Gly Thr Met
    290                 295                 300

Ser Pro Glu Ala Phe Leu Gln Glu Ala Gln Val Met Lys Lys Leu Arg
305                 310                 315                 320

His Glu Lys Leu Val Gln Leu Tyr Ala Val Val Ser Glu Glu Pro Ile
                325                 330                 335

Tyr Ile Val Thr Glu Tyr Met Ser Lys Gly Ser Leu Leu Asp Phe Leu
            340                 345                 350

Lys Gly Glu Thr Gly Lys Tyr Leu Arg Leu Pro Gln Leu Val Asp Met
        355                 360                 365

Ala Ala Gln Ile Ala Ser Gly Met Ala Tyr Val Glu Arg Met Asn Tyr
    370                 375                 380

Val His Arg Asp Leu Arg Ala Ala Asn Ile Leu Val Gly Glu Asn Leu
385                 390                 395                 400

Val Cys Lys Val Ala Asp Phe Gly Leu Ala Arg Leu Ile Glu Asp Asn
                405                 410                 415

Glu Tyr Thr Ala Arg Gln Gly Ala Lys Phe Pro Ile Lys Trp Thr Ala
            420                 425                 430

Pro Glu Ala Ala Leu Tyr Gly Arg Phe Thr Ile Lys Ser Asp Val Trp
        435                 440                 445

Ser Phe Gly Ile Leu Leu Thr Glu Leu Thr Thr Lys Gly Arg Val Pro
    450                 455                 460

Tyr Pro Gly Met Val Asn Arg Glu Val Leu Asp Gln Val Glu Arg Gly
465                 470                 475                 480

Tyr Arg Met Pro Cys Pro Pro Glu Cys Pro Glu Ser Leu His Asp Leu
```

-continued

```
                485                 490                 495
Met Cys Gln Cys Trp Arg Lys Glu Pro Glu Glu Arg Pro Thr Phe Glu
            500                 505                 510

Tyr Leu Gln Ala Phe Leu Glu Asp Tyr Phe
        515                 520
```

CYTOPLASMIC PROTEIN COMPLEX COMPRISING A KINASE SUBSTRATE SENSOR CELLS AND ASSOCIATED DETECTION METHODS

CROSS-REFERENCE TO RELATED APPLICATIONS

This application is a national phase entry under 35 U.S.C. § 371 of International Patent Application PCT/EP2012/053463, filed Feb. 29, 2012, designating the United States of America and published in English as International Patent Publication WO 2012/117031 A1 on Sep. 7, 2012, which claims the benefit under Article 8 of the Patent Cooperation Treaty and under 35 U.S.C. § 119(e) to Great Britain Patent Application Serial No. 1103453.5, filed Mar. 1, 2011, and to U.S. Provisional Patent Application Ser. No. 61/464,285, filed Mar. 1, 2011.

TECHNICAL FIELD

The disclosure relates to a cytoplasmic protein complex comprising (a) a first recombinant fusion protein comprising a kinase, fused to a first interaction polypeptide and (b) a second recombinant fusion protein comprising a domain comprising a reporter phosphorylation site, wherein the domain is fused to a second interaction polypeptide. It relates further to a method of detecting compound-compound-interaction using the cytoplasmic protein complex, and to cells comprising such cytoplasmic protein complex.

BACKGROUND

Protein-protein interactions are an essential key in all biological processes, from the replication and expression of genes to the morphogenesis of organisms. Protein-protein interactions govern, amongst others, ligand-receptor interaction and the subsequent signaling pathway; they are important in assembly of enzyme subunits, in the formation of biological supramolecular structures such as ribosomes, filaments and virus particles, and in antigen-antibody interactions.

Researchers have developed several approaches in attempts to identify protein-protein interactions. Co-purification of proteins and co-immunoprecipitation were amongst the first techniques used. However, these methods are tedious and do not allow high throughput screening. Moreover, they require lysis corrupting the normal cellular context. A major breakthrough was obtained by the introduction of the genetic approaches, of which the yeast two-hybrid (Fields and Song, 1989) is the most important one. Although this technique became widely used, it has several drawbacks. The fusion proteins need to be translocated to the nucleus, which is not always evident. Proteins with intrinsic transcription activation properties may cause false positives. Moreover, interactions that are dependent upon secondary modifications of the protein such as phosphorylation cannot be easily detected.

Several alternative systems have been developed to solve one or more of these problems.

Approaches based on phage display do avoid the nuclear translocation. WO9002809 describes how a binding protein can be displayed on the surface of a genetic package, such as a filamentous phage, wherein the gene encoding the binding protein is packaged inside the phage. Phages, which bear the binding protein that recognizes the target molecule, are isolated and amplified. Several improvements of the phage display approach have been proposed, as described, e.g., in WO9220791, WO9710330 and WO9732017.

However, all these methods suffer from the difficulties that are inherent at the phage display methodology: the proteins need to be exposed at the phage surface and are so exposed to an environment that is not physiologically relevant for the in vivo interaction. Moreover, when screening a phage library, there will be a competition between the phages that results in a selection of the high affinity binders.

U.S. Pat. No. 5,637,463 describes an improvement of the yeast two-hybrid system, whereby a phage library can be screened for modification-dependent protein-protein interactions. However, this method relies on the co-expression of the modifying enzyme, which will exert its activity in the cytoplasm and may modify enzymes other than the one involved in the protein-protein interaction, which may, on its turn, affect the viability of the host organism.

An interesting evolution is described in U.S. Pat. No. 5,776,689, by the so-called protein recruitment system. Protein-protein interactions are detected by recruitment of a guanine nucleotide exchange factor (Sos) to the plasma membrane, where Sos activates a Ras reporter molecule. This results in the survival of the cell that otherwise would not survive in the culture conditions used. Although this method certainly has the advantage that the protein-protein interaction takes place under physiological conditions in the submembranary space, it has several drawbacks. Modification-dependent interactions cannot be detected. Moreover, the method is using the pleiotropic Ras pathway, which may cause technical complications.

A major improvement in the detection of protein-protein interactions was disclosed in WO0190188, describing the so called Mappit system. The method, based on a cytokine receptor, allows not only a reliable detection of protein-protein interactions in mammalian cells, but also modification-dependent protein interactions can be detected, as well as complex three-hybrid protein-protein interactions mediated by a small compound (Caligiuri et al., 2006). However, although very useful, the system is limited in sensitivity and some weak interactions cannot be detected. Moreover, as this is a membrane-based system, nuclear interactions are normally not detected.

There is still a need for a sensitive identification system for compound-compound interactions that can study these interactions under physiological conditions, with a low background and by which modification-dependent protein-protein interactions can be isolated.

DISCLOSURE

The disclosure, based on a mutant cytoplasmic kinase, preferably a constitutive mutant cytoplasmic kinase, satisfies this need and provides additional advantages as well. Whereas Mappit is using a ligand-receptor-controlled inducible kinase to limit and correct for the background, the cytoplasmic kinase, especially the constitutive cytoplasmic kinase, is surprisingly giving a higher signal/noise ratio, allowing the detection of interactions that cannot be detected in the mappit system. The high signal/noise ratio is unexpected for a cytoplasmic system, as a person skilled in the art would expect that cytoplasmic kinase can move freely in the cytoplasm, and reach its substrate without other recruitment signals than the kinase and the phosphorylation domain. By using a cytoplasmic system, the problem of detecting nuclear protein-protein interactions has been solved. The unexpectedly high sensitivity of the present method allows detecting weak protein interactions, such as the p51/p51 interaction, which cannot be detected by Mappit. Alternatively, a mutant kinase inducible by an exogenous small compound can be used. This approach combines the advantages of the constitutive kinase, with the inducibility, without interfering with the endogenous pathways.

BRIEF DESCRIPTION OF THE DRAWING

FIG. 2A: Schematic overview of the assay. The first interacting polypeptide (X) is fused to the C-terminal region of Tyk2 comprising the kinase domain, whereas the second interacting polypeptide (Y) is fused to a fragment of gp130, which contains phosphorylation sites. When polypeptides X and Y interact, the Tyk2 kinase domain phosphorylates the phosphorylation sites of gp130. STAT3 transcription factors are recruited to these phosphorylated sites and are, in turn, phosphorylated by the Tyk2 kinase domain, which results in their activation. Dimers of activated STAT3 transcription factors are able to bind the specific rPAPI promoter, which drives the expression of a firefly luciferase reporter gene. The activity of this reporter gene is measured as light production in a luciferase detection assay using a luminometer. FIG. 2B: Application to the analysis of HIV1 RT subunits. Cells were transfected with the following plasmids: a) pMet7-HA-Tyk2(C)-RTp66+pMG2-RTp51+pXP2d2-rPAPI-luciferase, b) pMet7-HA-Tyk2(C)-RTp66+pMG2-RTp66+pXP2d2-rPAPI-luciferase, c) pMet7-HA-Tyk2(C)-RTp51+pMG2-RTp51+pXP2d2-rPAPI-luciferase. Luciferase activity is shown as fold induction relative to the luciferase activity measured in cells transfected with the same Tyk2(C) fusion, an unfused gp130 fragment and the luciferase reporter plasmid (pMet7-HA-Tyk2(C)-RTp66+pMG1+pXP2d2-rPAPI-luciferase in a) and b); pMet7-HA-Tyk2(C)-RTp51+pMG1+pXP2d2-rPAPI-luciferase in c). Error bars indicate standard deviation.

DETAILED DESCRIPTION

Figure 1:
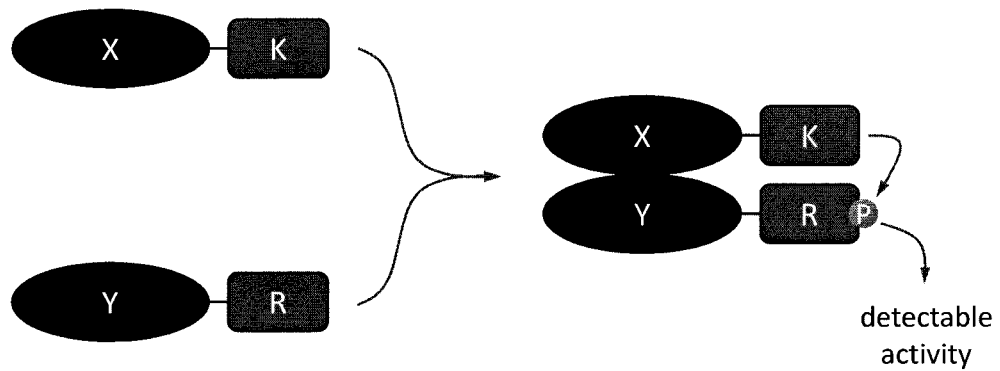
FIG. 1: Schematic representation of the cytoplasmic protein complex. A first interacting polypeptide (X) is fused to a constitutive kinase (K) and a second interacting polypeptide (Y) is fused to a reporter phosphorylation site (R). Interaction between the interacting polypeptides X and Y results in the reporter phosphorylation site being phosphorylated (P) by the constitutive kinase, leading to a detectable activity.

A first aspect hereof is a cytoplasmic protein complex comprising (a) a first recombinant fusion protein comprising a kinase fused to a first interaction polypeptide and (b) a second recombinant fusion protein comprising a domain comprising a reporter phosphorylation site, wherein the domain is fused to a second interaction polypeptide.

The first recombinant fusion protein need not comprise a reporter phosphorylation site. Preferably, the kinase is a mutant kinase, more preferably, a mutant tyrosine kinase. In one embodiment, the mutant tyrosine kinase is a constitutive kinase. In another embodiment, the mutant tyrosine kinase is an inactive mutant that is activated by addition of an exogenous small molecule. Such mutant kinase is known to the person skilled in the art, and has been described, as a non-limiting example, by Qiao et al. (2006) as a Src 388R/A mutant or a 391R/A mutation in the corresponding human Src protein (Accession number NP_938033, version NP_938033.1). Alternatively, it may be a similar mutation in the Jak kinase family, such as, but not limited to Tyk2 1027R/A.

In one embodiment, the kinase is a constitutive kinase mutant derived from Tyk2, such as, but not limited to, a constitutive Tyk2 deletion mutant and/or a Tyk2 V678F mutant. "Derived from Tyk2" as used herein means that the kinase is a part of the human Tyk2 non-receptor tyrosine-protein kinase (Genbank accession number NP_003322; version NP_003322.3; SEQ ID NO:26) or a mutant or variant thereof, wherein the part shows constitutive kinase activity. A variant, as a non-limiting example, is a homologue, paralogue or orthologue. "Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. "Orthologues" and "paralogues" encompass evolutionary concepts used to describe the ancestral relationships of genes. "Paralogues" are genes within the same species that have originated through duplication of an ancestral gene; "orthologues" are genes from different organisms that have originated through speciation, and are also derived from a common ancestral gene. Preferably, the homologue, "orthologue" or "paralogue" has a sequence identity at protein level of at least 50%, 51%, 52%, 53%, 54% or 55%, 56%, 57%, 58%, 59%, preferably 60%, 61%, 62%, 63%, 64%, 65%, 66%, 67%, 68%, 69%, more preferably 70%, 71%, 72%, 73%, 74%, 75%, 76%, 77%, 78%, 79%, even more preferably 80%, 81%, 82%, 83%, 84%, 85%, 86%, 87%, 88%, 89%, and most preferably 90%, 91%, 92%, 93%, 94%, 95%, 96%, 97%, 98%, 99% or more as measured in a BLASTp (Altschul et al., 1997; Altschul et al., 2005). Variants and parts thereof according to the invention do show kinase activity. Preferably, the part is a part with constitutive kinase activity, preferably fragment 589-1187 of SEQ ID NO:26. Alternatively, the part is the part corresponding to fragment 589-1187 of SEQ ID NO:26 in a homologue, paralogue or orthologue as defined above, wherein the part has constitutive kinase activity. In an alternative embodiment, the constitutive kinase is a constitutive kinase derived from a Jak kinase, preferably from a Jak kinase selected from the group consisting of Jak1 (Accession number P23458, version P23458.2), Jak2 (Accession number O60674, version O60674.2), and Jak3 (Accession number P52333, version P52333.2), or a mutant or variant thereof as defined above. Preferably, the constitutive kinase is a constitutive Jak2 deletion mutant. In still another alternative embodiment, the constitutive kinase is a constitutive kinase derived from a Src kinase (Accession number NP_005408, version NP_005408.1) or a mutant or variant thereof as defined above. Preferably, the constitutive kinase is a Src deletion mutant as depicted in SEQ ID NO:27. "Derived" as used herein means that the kinase is a part of the cited non-receptor tyrosine-protein, or from a mutant or variant thereof, wherein the part shows constitutive kinase activity.

In one embodiment, the first recombinant fusion protein comprises SEQ ID NO:1 (pseudo kinase+kinase). In another embodiment, the first recombinant protein comprises SEQ ID NO:2 (kinase). In still another embodiment, the first recombinant protein comprises a sequence selected from the group consisting of SEQ ID NO:5, SEQ ID NO:6, SEQ ID NO:7, and SEQ ID NO:27. In one embodiment, the second recombinant fusion protein comprises SEQ ID NO:3 (STAT site). In another embodiment, the second recombinant fusion protein comprises SEQ ID NO:4. Most preferably, the cytoplasmic protein complex comprises a first recombinant fusion protein comprising SEQ ID NO:1 or SEQ ID NO:2 and a second recombinant fusion protein comprising SEQ ID NO:3 or SEQ ID NO:4.

In cases where an inactive mutant is used that can be activated by a small compound, one preferred embodiment is a mutant kinase whereby the mutant kinase is a Src 388R/A mutation or a 391R/A mutation in the corresponding human Src protein (Accession number NP_938033, version NP_938033.1). Another embodiment is a mutant wherein the mutant kinase is a Tyk2 1027R/A mutant (numbering of SEQ ID NO:26). Preferably, the small compound is imidazole.

The kinase of the first recombinant fusion protein is fused to a first interaction polypeptide, as defined below. The fusion may occur at the amino-terminal end, at the carboxy-terminal end, or internal in the recombinant polypeptide. In cases of kinases consisting of two domains, the first interaction polypeptide may even occur as an internal fusion in between the two domains. The domain comprising the reporter phosphorylation site of the second recombinant fusion protein is fused to a second interaction polypeptide, as defined below. The fusion may occur at the amino-terminal end, at the carboxy-terminal end, or internal in the recombinant polypeptide. The first recombinant fusion protein may not comprise a reporter phosphorylation site. The first recombinant fusion protein, the second recombinant fusion protein or both may further comprise other sequences such as, but not limited to, a localization signal to direct the cytoplasmic complex to a specific organelle into the cytoplasm of the cell, or to the nucleus.

Preferably, the cytoplasmic protein complex is phosphorylated at the reporter phosphorylation site; even more preferably, the phosphorylation is carried out by the kinase.

In an embodiment, the protein complex according to the invention is assembled by direct interaction of the first interaction polypeptide with the second interaction polypeptide. The first and the second interaction protein may be identical, in cases where homodimerization is studied. However, the protein complex is not limited to two compounds, and the interaction may be mediated by one or more other compounds. As a non-limiting example, the first interaction polypeptide may bind a protein that is bound on its turn by the second interaction polypeptide. Instead of a protein, the bridging compound can be one or more molecules of non-proteinous nature, or mixtures of small compounds and proteins. Another non-limiting example is a protein complex, wherein a small compound binding to the first, as well as to the second, interaction polypeptide.

The complex formation may be dependent upon modification of the first and/or second interaction polypeptide. Modification can be, but is not limited to, presence or absence of phosphorylation, acetylation, acylation, methylation, ubiquitinilation or glycosylation, or occurrence of proteolytic cleavage or not, or a combination thereof. Preferably, modification is carried out by a modifying enzyme (as defined below). Preferably, the modifying enzyme is fused to the first and/or second recombinant fusion protein. In case of phosphorylation, the modifying enzyme may be the constitutive kinase fused to the first interaction polypeptide, as described above.

Another aspect hereof is a method for detecting compound-compound interaction comprising (a) fusing a cytoplasmic kinase to a first interaction polypeptide resulting in a first recombinant fusion protein (without reporter phosphorylation site) according to the invention; (b) fusing a domain comprising a reporter phosphorylation site to a second interaction polypeptide, resulting in a second recombinant fusion protein according to the invention; (c) expressing both recombinant fusion proteins in a cell; and (d) identifying and/or selecting those cells in which the reporter phosphorylation site is phosphorylated.

Preferably, the kinase is a mutant kinase, even more preferably, a mutant tyrosine kinase. In one embodiment, the mutant kinase is a constitutive kinase; even more preferably, the kinase is a constitutive mutant derived from a Tyk2 kinase, preferably a deletion mutant or a constitutive V678F mutant. Alternatively, a constitutive Jak2 deletion mutant or a constitutive Src kinase deletion mutant can be used. In another embodiment, kinase is an inactive mutant kinase that is activated by addition of an exogenous small compound. Such mutant kinase is known to the person skilled in the art and has been described, as a non-limiting example, by Qiao et al. (2006).

In one embodiment, the first recombinant fusion protein comprises SEQ ID NO:1. In another embodiment, the first recombinant fusion protein comprises SEQ ID NO:2. In still another embodiment, the first recombinant protein comprises a sequence selected from the group consisting of SEQ ID NO:5, SEQ ID NO:6, SEQ ID NO:7, and SEQ ID NO:27. In one preferred embodiment, the second recombinant fusion protein comprises SEQ ID NO:3. In another preferred embodiment, the second recombinant fusion protein comprises SEQ ID NO:4. Most preferably, the cytoplasmic protein complex comprises a first recombinant fusion protein comprising SED ID NO:1 or SEQ ID NO:2 and a second recombinant fusion protein comprising SEQ ID NO:3 or SEQ ID NO:4.

The gene encoding the first and/or the second recombinant fusion protein may be placed downstream and is either a constitutive or an inducible promoter. The latter construction may have some advantages in cases where there is a competition for the binding site between interaction polypeptide and endogenous polypeptides. Induction of the recombinant fusion protein comprising the first interaction polypeptide in the presence of the second interaction polypeptides may facilitate the binding and avoid saturation of the binding sites with endogenous polypeptides. The cell may be any cell including, but not limited to, bacterial cells, fungal cells, yeast cells, insect cells and mammalian cells. Preferably, the cell is a eukaryotic cell; even more preferably, the cell is a mammalian cell. In cases where homodimerization is studied, the first and the second interaction protein may be identical. In this case, the same protein is fused to the kinase at one hand, and to a domain comprising the reporter phosphorylation site at the other hand.

The first recombinant fusion protein and the second recombinant fusion protein may be situated on one or on separated vectors. The vector used for transformation and expression of the first and/or second recombinant polypeptide can be any vector known to the person skilled in the art including, but not limited to, episomal vectors, integrative vectors and viral vectors.

In an embodiment, a eukaryotic cell carrying a gene encoding a first recombinant fusion protein is transformed or transfected with a vector library encoding second recombinant fusion proteins hereof. Interaction of the first interaction polypeptide with the second interaction polypeptide will result in phosphorylation of the reporter phosphorylation site and can be detected by the use of a reporter system. One specific embodiment of the method to detect compound-compound binding is a method whereby the compounds are proteins and binding is a protein-protein interaction. Another specific embodiment is a method to detect protein-protein interaction, whereby the interaction is modification state dependent, and modification is carried out by a modifying enzyme. Still another specific embodiment is a method to detect compound-compound binding, whereby binding is mediated by three or more partners. In this case, one or more partners may not be, or not completely be, of proteinous nature. It is clear for a person skilled in the art that the first interaction polypeptide may, as a non-limiting example, bind to a small molecule. On the other hand, the second interaction polypeptide may also bind to the small molecule, so that the first and the second are linked together by the small molecule. The small molecule may be present in the host cell, as a compound produced by the cell itself, or as a compound that is taken up from the medium.

Preferably, the method to detect compound-compound binding comprises the construction of a eukaryotic cell comprising a first recombinant fusion protein hereof, followed by transformation or transfection of the cell by a library of vectors encoding second recombinant fusion proteins according to the invention. The compound-compound binding is detected by the phosphorylation of the reporter phosphorylation site. Detection of the phosphorylation of the complex can be realized by isolation of the complex and analyzing the phosphorylation (e.g., by using radioactive labeled phosphor). Preferably, phosphorylation of the reporter phosphorylation site is resulting in the induction of a reporter system. A reporter system can be any system that allows the detection and/or the selection of the cells carrying a phosphorylated cytoplasmic protein complex according to the invention. It is clear for the person skilled in the art that several reporter systems can be used. As a non-limiting example, phosphorylation may lead to the induction of a signaling pathway, and a luciferase gene; an antibiotic resistance gene or a cell surface marker gene can be placed under control of a promoter that is induced by the signaling pathway. Alternatively, reporter systems may be used that are based on the change in characteristics of compounds of the signaling pathway, when the pathway is active, such as the phosphorylation and/or dimerization of such compounds. Still another possibility is using antibodies and/or other binding polypeptides which specifically recognize the phosphorylated reporter phosphorylation site.

One embodiment is a reporter phosphorylation site that is part of a Signal Transducer and Activator of Transcription (STAT) binding site, most preferentially, part of a STAT1 and/or STAT3 binding site. In this case, the reporter gene can be placed under the control of a STAT-inducible promoter, such as, but not limited to, the Pancreatitis Associated Protein 1 (rPAP) promoter. Alternatively, as phosphorylation of the reporter phosphorylation site will result in binding of a STAT polypeptide to the phosphorylated reporter phosphorylation site, followed by phosphorylation of the STAT polypeptide and subsequent dimerization of two phosphorylated STAT molecules, the dimerization itself can be used as reporter signal. Still another alternative reporter system consists of a protein complementation assay, wherein one part of the protein is incorporated in or associated with the cytoplasmic protein complex according to the invention, and the second part of the protein is recruited to the phosphorylated reporter phosphorylation site, leading to a detectable activity of the reconstituted protein.

Still another aspect hereof is a cell comprising a cytoplasmic protein complex according to the invention. This cell may be any cell including, but not limited to, bacterial cells, fungal cells, yeast cells, insect cells and mammalian cells. Preferably, the cell is a eukaryotic cell; even more preferably, the cell is a mammalian cell. Preferably, the reporter phosphorylation site in the cytoplasmic protein complex is phosphorylated. Preferably, the cell also comprises a reporter system, allowing the detection of the phosphorylation of the reporter phosphorylation site of the cytoplasmic protein complex.

Still another aspect hereof is a method for detecting compounds disrupting a polypeptide-polypeptide interaction, the method comprising (a) growing a cell comprising a protein complex according to the invention, wherein the cytoplasmic protein complex comprises the polypeptide-polypeptide interaction that one wants to disrupt, in absence and in presence of at least one compound; (b) comparing the phosphorylation of the reporter phosphorylation site in the second recombinant fusion protein of the cytoplasmic protein complex of cells, grown in presence or absence of the compound; and (c) identifying and/or selecting those cells wherein the reporter phosphorylation site is not phosphorylated. It is clear for the person skilled in the art that the polypeptide-polypeptide interaction as mentioned above may be an indirect interaction by three of more partners, whereby even one or more of the partners may not be of proteinous nature.

Definitions

The following definitions are set forth to illustrate and define the meaning and scope of various terms used to describe the invention herein.

"Protein" as used herein means a chain composed of amino acids, independent of the length. The terms "protein" and "polypeptide" are interchangeable. The protein can be modified by modifications such as, but not limited to, phosphorylation, glycosylation, ubiquitinilation and acetylation.

"Domain" as used herein is a part of a polypeptide, wherein the part may carry a specific function, such as, but not limited to, an enzymatic center or a phosphorylation site.

"Protein complex" as used herein means a structure that comprises at least two, non-covalently linked, protein molecules. Protein complexes can consist of more than two proteins and include other molecules that are not proteins. Some non-limiting examples of such molecules are metal ions, ATP, or carbohydrate molecules.

"Cytoplasmic protein complex" means that the protein complex as described above moves freely in the cytoplasm of the cell and is not linked to the cell membrane. However, the cytoplasmic protein complex may be directed to the nucleus or cytoplasmic organelles, using localization signal sequences.

A "kinase" as used herein is a polypeptide that can transfer a phosphate group to an amino acid of the same or another polypeptide. Preferably, the amino acid is a serine, a threonine or a tyrosine. Even more preferably, the amino acid is embedded in a phosphorylation site.

A "phosphorylation site" as used herein is a pattern of several amino acids, preferably comprising a serine, threonine or a tyrosine, and determining the amino acid that will be phosphorylated by the kinase. Most kinases can occur in an inactive state and/or in an active state, wherein the reporter phosphorylation site is only phosphorylated in the active state of the kinase. Kinases can be switched from the inactive form to the active form by phosphorylation, or by other modifications, such as proteolysis, or by mutation. The phosphorylation can be autophosphorylation, cross-phosphorylation (by a protein complex of identical kinases) or by action of another kinase.

A "cytoplasmic kinase" is a kinase that is freely moving in the cytoplasm, and not linked or recruited to the cellular membrane. The cytoplasmic kinase according to the invention may be derived from a membrane-linked kinase, by deleting the membrane anchoring or membrane recruitment domain, without loss of the enzymatic kinase activity.

A "mutant kinase" is a kinase of which the sequence differs from the sequence that occurs normally in nature, by the replacement, deletion or insertion of one or more amino acids. Homologues, orthologues and paralogues are not considered as mutants, as they are present as a normal form in nature.

"Constitutive" as used herein means that the kinase is continuously in the active state, normally as a consequence of a mutation, or by proteolytic cleavage removing an inhibitor. Constitutive kinases are known to the person skilled in the art and comprise, but are not limited to, truncated forms of Tyk2, truncated forms of Src kinase and point mutations such as Tyk2 (V678F), Jak1 (V658F) and Jak2(V617F).

An "inactive kinase mutant" means that that the mutant form shows a kinase activity that is significantly lower than the original non-mutated form. Preferably, the remaining activity is lower than 50% of the original activity, more preferably lower than 20%, even more preferably lower than 10%, and most preferably lower than 5% of the original activity.

"Activated by the addition of an exogenous small compound" as used herein means that the activity of the inactive kinase is partly or totally restored by addition of a small compound to the cells, whereby the small compound, exogenous to the cell, is taken up by the cell and activates the kinase as an intracellular exogenous compound. "Activated by the addition of an exogenous small compound" is used to make a distinction with ligand-receptor-induced activation, where a ligand is binding to the extracellular part of a receptor, and induces activation of the kinase.

"Exogenous" as used herein means that the compound is normally not present in the cell.

"Reporter phosphorylation site" is the site that is phosphorylated in the protein complex upon interaction of the first and the second interaction polypeptide; it is distinct from a possible phosphorylation site in the kinase domain that is autophosphorylated in the constitutive kinase.

"First interaction polypeptide" as used herein is a polypeptide of which one wants to study the interaction with one or more compounds. The first interaction polypeptide is normally referred to as a "bait" in the two-hybrid terminology.

"Second interaction polypeptide" as used herein is a polypeptide that is presented to study its interaction with the first interaction polypeptide. The second interaction polypeptide is normally referred to as a "prey" in the two-hybrid terminology. It is clear for the person skilled in the art that the first and the second interaction polypeptide are interchangeable in the invention, in this respect that either a "bait" or "prey" may be fused to constitutive kinase hereof. Indeed, the resulting protein complex will have an identical overall composition, composed of the four essential elements (first interaction polypeptide, second interaction polypeptide, constitutive kinase and reporter phosphorylation site), and independent whether the first interaction polypeptide is fused to the constitutive kinase or the reporter phosphorylation site (wherein the second interaction polypeptide is then fused to the reporter phosphorylation site and the constitutive kinase, respectively), the interaction of the first with the second interacting polypeptide will lead to the formation of a cytoplasmic protein complex according to the invention, and will result in the phosphorylation of the reporter phosphorylation site. In one preferred embodiment, the first and the second interaction proteins are identical to study homodimerization or homomultimerization of a protein. In another preferred embodiment, the first and the second proteins are different, allowing the study of protein-protein interactions of heterodimers or heteromultimers.

"Modifying enzyme" as used herein means any enzymatic activity that results in a modification of the first and/or second interaction polypeptide. Such modification can be, as a non-limiting example, phosphorylation, acetylation, acylation, methylation, ubiquitinilation or glycosylation, occurrence of proteolytic cleavage, or a combination thereof. Preferably, the modification is phosphorylation. The modifying enzyme may be associated to or incorporated in the first and/or the second recombinant fusion protein of the cytoplasmic protein complex. It may be co-expressed, with the first and/or second interaction polypeptide, or it can be fused to one or both of the polypeptides. In case of phosphorylation, the constitutive kinase of the cytoplasmic protein complex according to the invention may carry out both the phosphorylation of the activation site as well as the phosphorylation of one or both of the interaction polypeptides.

"Compound" means any chemical or biological compound, including simple or complex organic or inorganic molecules, peptides, peptido-mimetics, proteins, antibodies, carbohydrates, nucleic acids or derivatives thereof.

"Interaction" means any interaction, be it direct or indirect. A direct interaction implies a contact between the interaction partners. An indirect interaction means any interaction whereby the interaction partners interact in a complex of more than two compounds. This interaction can be completely indirect, with the help of one or more bridging compounds, or partly indirect, where there is still a direct contact that is stabilized by the interaction of one or more compounds.

EXAMPLES

Materials and Methods to the Invention

Plasmids Used in the Examples

A first type of plasmids express chimeric proteins consisting of an HA-tagged C-terminal portion of human Tyk2 fused at its C-terminus to the first interacting polypeptide and are generated in the pMet7 vector, which contains a strong constitutive hybrid SRα promoter (Takebe et al., 1988). To generate the pMet7-HA-Tyk2(C)-RTp66 plasmid, the sequence encoding the C-terminal end of human Tyk2 comprising the kinase domain (starting from amino acids 589 and omitting the stop codon) was amplified by PCR on cDNA from HEK293 cells with primers MBU-O-6486 and MBU-O-6487. In addition to an HA coding sequence, the former primer contained an ApaI restriction enzyme recognition site, whereas the latter primer contained an EcoRI restriction enzyme recognition site. The PCR amplicon was digested with ApaI and EcoRI and ligated in the ApaI-EcoRI cut pMG2-RTp66 plasmid (a pMet7-derived plasmid encoding a Flag-gp130-RTp66 chimeric protein), which contained ApaI and EcoRI sites flanking the sequences encoding the Flag-gp130 fusion protein at the 5' and 3' end, respectively (Pattyn et al., 2008). pMet7-HA-Tyk2(C)-RTp51 was generated by exchanging the RTp51 insert from pMG2-RTp51 (Pattyn et al., 2008) with RTp66 from pMet7-HA-Tyk2(C)-RTp66 using the EcoRI and NotI sites that flank these inserts at the 5' and 3' end, respectively. Full length human LEDGF was PCR amplified on cDNA from HeLa cells using primers MBU-O-3879 and MBU-O-3880 and exchanged with the RTp66 insert of pMet7-HA-Tyk2(C)-RTp66 using EcoRI and NotI restriction sites to generate pMet7-HA-Tyk2(C)-LEDGF. Similarly, the full-length human MDM2 sequence was PCR amplified on an MDM2 entry clone from the hORFeome collection (Lamesch et al., 2007) with primers MBU-O-3912 and MBU-O-3913 and exchanged with EcoRI-NotI to produce pMet7-HA-Tyk2(C)-MDM2. The N-terminal region of human p53 (amino acids 2-72) was PCR amplified on a p53 entry clone from the hORFeome collection (Lamesch et al., 2007) with primers MBU-O-2277 and MBU-O-2273 and exchanged using EcoRI and NotI restriction enzymes, yielding pMet7-HA-Tyk2(C)-p53 (N). The plasmid pMet7-HA-Jak2(C)-RTp66 was generated by PCR amplifying the sequence encoding the C-terminal end of mouse Jak2 (from amino acid 535 until the end of the protein, leaving the stop codon out) on pRK5-mJak2 (Silvennoinen et al., 1993) with primers MBU-O-6653 and MBU-O-6655. This fragment was exchanged with the sequence encoding Tyk2(C) from pMet7-HA-Tyk2(C)-RTp66 through a PacI-EcoRI restriction digest. Likewise, the coding sequence for the kinase domain of c-Src (amino acids 266-523) was PCR amplified on a c-Src entry clone from the hORFeome collection (Lamesch et al., 2007) with primers MBU-O-6656 and MBU-O-6657 and exchanged using PacI and EcoRI restriction enzymes, generating pMet7-HA-c-Src(K)-RTp66. The pMet7-HA-Tyk2 (R1027A)-RTp66 plasmid was generated by first PCR amplifying the human Tyk2 sequence on HEK293 cDNA with primers MBU-O-7811 and MBU-O-7812 and exchanging the resulting amplicon for the Tyk2(C) sequence of pMet7-HA-Tyk2(C)-RTp66 using PacI and EcoRI restriction enzymes to yield pMet7-HA-Tyk2-RTp66. Next, the R1027A mutation was introduced by site-directed mutagenesis using primers MBU-O-7341 and MBU-O-7342.

The plasmids encoding the fusions with the second interacting polypeptide were of the type also used in MAPPIT, designated pMG1 and pMG2 (WO0190188, Eyckerman et al., 2001; Lemmens et al., 2003). These plasmids encode fusion proteins of the second interacting polypeptide coupled to a fragment of the human gp130 cytokine receptor chain, which contains multiple tyrosine residues that, upon phosphorylation, make up recruitment sites for STAT3. RTp66 and RTp51 containing plasmids pMG2-RTp66 and pMG2-RTp51 have been described elsewhere (Pattyn et al., 2008). The pMG1 plasmid encoding an unfused gp130 receptor fragment was obtained by cutting out the MAPPIT prey insert of a pMG1 vector using EcoRI and XhoI, blunting the vector backbone through Pfu DNA Polymerase and self-ligation. The pMG2-IN plasmid was constructed by PCR amplifying the sequence encoding HIV1 integrase on the pNL4-3 plasmid template (Adachi et al., 1986) using primers MBU-O-3813 and MBU-O-3814 and exchanging this sequence with the insert of a pMG2 MAPPIT vector using EcoRI and NotI restriction enzymes. Similarly, the coding region of human MDM2 was PCR amplified with primers MBU-O-3912 and MBU-O-3913 and exchanged with EcoRI-NotI to produce pMG2-MDM2. pMG1-p53 and pMG1-EFHA1 were generated by Gateway recombination mediated transfer of the full-length sequences of human p53 and EFHA1 from entry vectors of the hORFeome collection (Lamesch et al., 2007) into a Gateway-compatible version of the pMG1 vector as described earlier (Lievens et al., 2009).

The reporter plasmid pXP2d2-rPAPI-luciferase used in the examples contains the STAT3-dependent rPAPI (rat Pancreatitis-Associated Protein I) promoter driving a firefly luciferase reporter gene as described previously (WO0190188, Eyckerman et al., 2001).

Transfection Procedure

Transfections were carried out using a standard calcium phosphate method. HEK293-T cells were seeded in black tissue-culture treated 96-well plates at 10,000 cells/well in 100 µl culture medium (DMEM supplemented with 10% FCS). Twenty-four hours later, plasmid DNA mixes were prepared that contained plasmids encoding fusion proteins with the first and second interacting proteins and reporter plasmids. The DNA was supplemented with 10 µl 2.5M $CaCl_2$ and double distilled water to a final volume of 100 µl. This mixture was added dropwise to 100 µl 2×HeBS buffer (280 mM NaCl, 1.5 mM $Na_2HPO_4$, 50 mM Hepes; pH 7.05) while vigorously vortexing. After incubation at room temperature for 15 minutes to allow DNA precipitates to form, the solution was added to the cells at 10 µl/well. Cells were incubated at 37° C., 8% $CO_2$. Forty-eight hours after transfection, luciferase activity was measured using the Luciferase Assay System kit (Promega) on a TopCount luminometer (Perkin-Elmer). Each transfection was done in triplicate and the average of the luciferase activity readings was used in the calculations.

A Nutlin-3 (Sigma) stock solution of 20 mM in DMSO was diluted in culture medium and added to the cells 24 hours after transfection. Imidazole (Sigma) diluted in culture medium was added to the cells 24 hours after transfection.

Figure 2A:
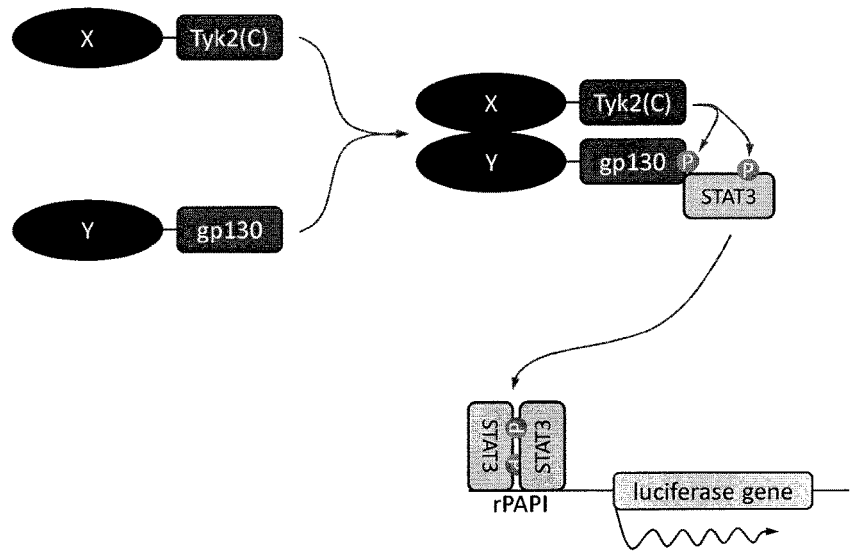
FIGS. 2A and 2B: Detection of the interaction between HIV1 Reverse Transcriptase (RT) subunits in an assay variant that comprises mutant Tyk2 kinase fusion proteins.
Figure 2B:
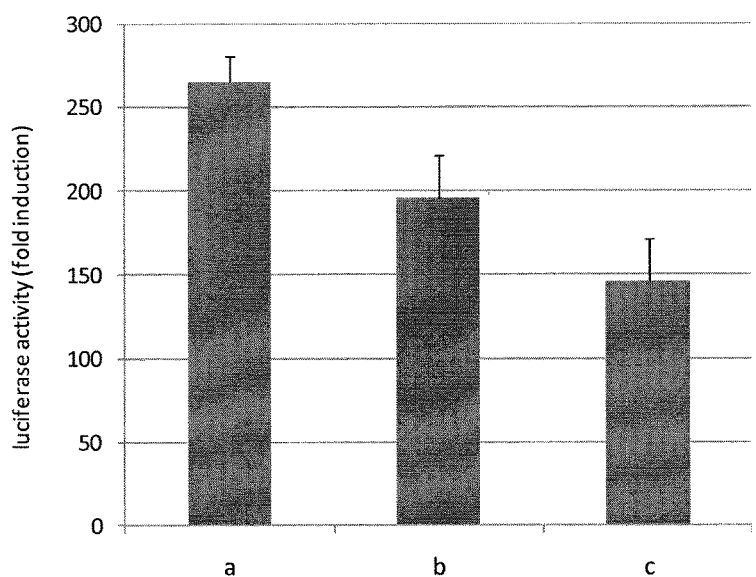

Background signal for each Tyk2(C) fusion polypeptide was determined by transfecting the plasmid that encodes it together with a plasmid encoding an unfused gp130 fragment (pMG1) and the luciferase reporter plasmid (pMet7-HA-Tyk2(C)-RTp66+pMG1+pXP2d2-rPAPI-luciferase in a) and b); pMet7-HA-Tyk2(C)-RTp51+pMG1+pXP2d2-rPAPI-luciferase in c)). The fold induction for each tested interaction was calculated as the ratio of the luciferase activity measured relative to the luciferase activity measured for the corresponding background signal. The results (FIG. 2A) show clear signals for both RT homo- and heterodimers. The strongest signal was that for the p66-p51 heterodimer;

| Oligonucleotide primer code | SEQ ID NO: | Sequence (5' > 3') |
|---|---|---|
| MBU-O-6486 | 8 | CCCGGGCCCACCATGTATCCATATGATGTTCCAGATTATGCTTTAATTAAAATCACCCAGCTGTCCCACTTGG |
| MBU-O-6487 | 9 | GGGGAATTCGCACACGCTGAACACTGAAGG |
| MBU-O-3879 | 10 | CGTACGAATTCGGGAGCTCGATGACTCGCGATTTCAAACCTGGAG |
| MBU-O-3880 | 11 | GGTCATCTAGACCGCGGCCGCTCAGTTATCTAGTGTAGAATCCTTCAG |
| MBU-O-3912 | 12 | GCGGAATTCATGTGCAATACCAACATGTCTG |
| MBU-O-3913 | 13 | CGCGCGGCCGCCTAGGGGAAATAAGTTAGCAC |
| MBU-O-2277 | 14 | GCGAGAATTCGAGGAGCCGCAGTCAGATCC |
| MBU-O-2273 | 15 | CGCTGCGGCCGCTTAGCGGGGAGCAGCCTCTGGC |
| MBU-O-6653 | 16 | CCCGCGGCCGCTTTAATTAAAATGGTGTTTCACAAAATCAG |
| MBU-O-6655 | 17 | GGGCTCGAGGAATTCCGCAGCTATACTGTCCCGG |
| MBU-O-6656 | 18 | CCCGCGGCCGCTTTAATTAAACCTCGGGAGTCGCTGCGGC |
| MBU-O-6657 | 19 | GGGCTCGAGGAATTCGAAGTAGTCCTCCAGGAAGG |
| MBU-O-3813 | 20 | CGTACGAATTCGGGAGCTCGTTTTTAGATGGAATAG |
| MBU-O-3814 | 21 | GGTCATCTAGACCGCGGCCGCTCAATCCTCATCCTGTCTAC |
| MBU-O-7811 | 22 | CATTTAATTAAACCTCTGCGCCACTGGGGG |
| MBU-O-7812 | 23 | CATGAATTCGCACACGCTGAACACTGAAGGG |
| MBU-O-7341 | 24 | CCGAGACCTAGCCGCGGCCAACGTGCTGC |
| MBU-O-7342 | 25 | GCAGCACGTTGGCCGCGGCTAGGTCTCGG |

Example 1: Detection of the Interaction Between HIV1 Reverse Transcriptase (RT) Subunits In order to determine the functionality of the assay, the interaction between HIV1 subunits that form homo- and heterodimers was tested by transfecting the following combinations of plasmids (100 ng of the Tyk2(C) fusion construct, 1 µg of the gp130 fusion construct and 50 ng of the luciferase reporter construct) according to the methods described above:
  a) pMet7-HA-Tyk2(C)-RTp66+pMG2-RTp51+pXP2d2-rPAPI-luciferase
  b) pMet7-HA-Tyk2(C)-RTp66+pMG2-RTp66+pXP2d2-rPAPI-luciferase
  c) pMet7-HA-Tyk2(C)-RTp51+pMG2-RTp51+pXP2d2-rPAPI-luciferase lower, but still robust, signals were obtained for the p66 and p51 homodimers. This trend corresponds to the affinities measured for p66-p51, p66-p66 and p51-p51 interactions in in vitro interaction assays, which were reported to be 0.3 µM, 4 µM and 230 µM, respectively (Venezia et al., 2006). These data illustrate the high sensitivity of the method.

Example 2: Interaction Between Nuclear Proteins

Figure 3:
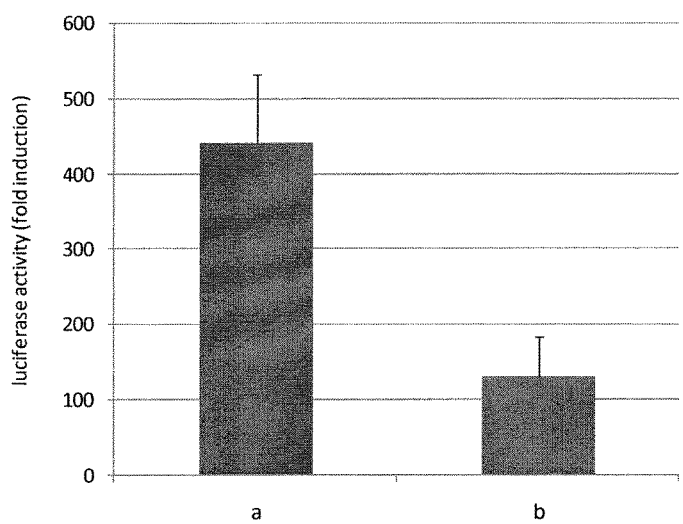
FIG. 3: Detection of the interaction between HIV1 Integrase (IN) and human lens epithelium-derived growth factor ("LEDGE") and between human p53 and mouse double minute 2 homolog ("MDM2"). Cells were transfected with the following plasmids: a) pMet7-HA-Tyk2(C)-LEDGF+pMG2-IN+pXP2d2-rPAPI-luciferase and b) pMet7-HA-Tyk2(C)-MDM2+pMG1-p53+pXP2d2-rPAPI-luciferase. Luciferase activity is shown as fold induction relative to the luciferase activity measured in cells transfected with the same Tyk2(C) fusion, an unfused gp130 fragment and the luciferase reporter plasmid (pMet7-HA-Tyk2(C)-LEDGF+pMG1+pXP2d2-rPAPI-luciferase in a); pMet7-HA-Tyk2(C)-MDM2+pMG1+pXP2d2-rPAPI-luciferase in b)). Error bars indicate standard deviation.

To determine whether the method can detect interactions between nuclear proteins, we tested the interaction between HIV1 Integrase (IN) and human LEDGF and between human p53 and MDM2, proteins with a nuclear localization. Cells were transfected with the following combinations of plasmids (250 ng of the Tyk2(C) fusion construct, 500 ng of the gp130 fusion construct and 50 ng of the luciferase reporter construct) according to the methods described above:
a) pMet7-HA-Tyk2(C)-LEDGF+pMG2-IN+pXP2d2-rPAPI-luciferase
b) pMet7-HA-Tyk2(C)-MDM2+pMG1-p53+pXP2d2-rPAPI-luciferase Background signal for each Tyk2(C) fusion polypeptide was determined by transfecting the plasmid that encodes it together with a plasmid encoding an unfused gp130 fragment (pMG1) and the luciferase reporter plasmid (pMet7-HA-Tyk2(C)-LEDGF+pMG1+pXP2d2-rPAPI-luciferase in a); pMet7-HA-Tyk2(C)-MDM2+pMG1+pXP2d2-rPAPI-luciferase in b)). The fold induction for each tested interaction was calculated as the ratio of the luciferase activity measured relative to the luciferase activity measured for the corresponding background signal. The result (FIG. 3) shows that these interactions give rise to strong signals, indicating that the method is able to detect interactions in the nucleus.

Example 3: Dose-Dependent Disruption of the Interaction Between Human p53 and MDM2 by Nutlin-3

Figure 4:
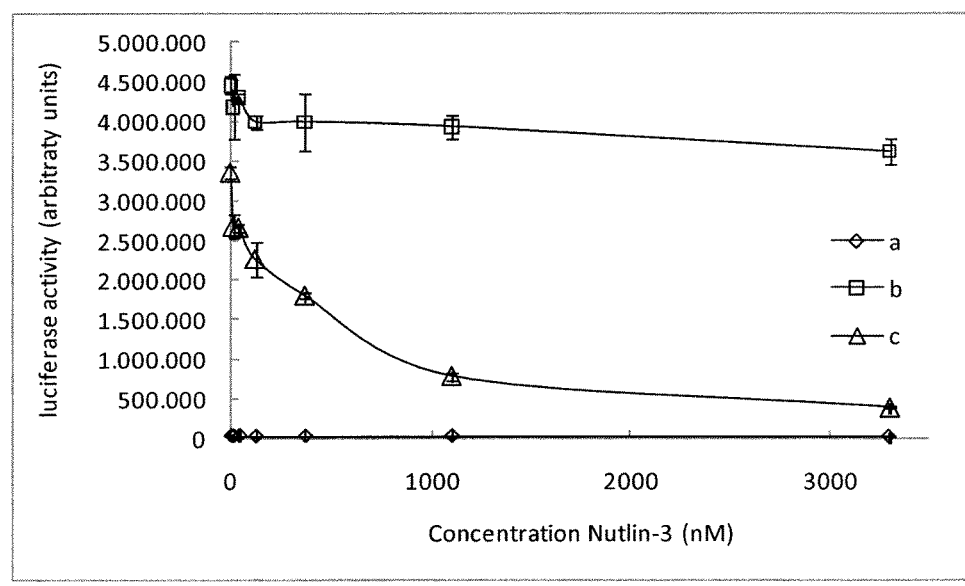
FIG. 4: Dose-dependent disruption of the interaction between human p53 and MDM2 by Nutlin-3. Cells were transfected with the following plasmids: a) pMet7-HA-Tyk2(C)-p53(N)+pMG1+pXP2d2-rPAPI-luciferase; b) pMet7-HA-Tyk2(C)-p53(N)+pMG1-EFHA1+pXP2d2-rPAPI-luciferase; and c) pMet7-HA-Tyk2(C)-p53(N)+pMG2-MDM2+pXP2d2-rPAPI-luciferase. After transfection, cells were treated with 0-14-41-123-370-1111-3333 nM Nutlin-3, final concentration. Error bars indicate standard deviation.

To show that the method can detect modulation of protein-protein interactions by small molecules, we analyzed the interaction between p53 and MDM2, which has been reported to be disrupted by Nutlin-3, a member of the nutlin family of potential novel anti-cancer compounds (Vassilev et al., 2004). Cells were transfected with the following combinations of plasmids (100 ng of the Tyk2(C) fusion construct, 1000 ng of the gp130 fusion construct and 50 ng of the luciferase reporter construct) according to the methods described above:
a) pMet7-HA-Tyk2(C)-p53(N)+pMG1+pXP2d2-rPAPI-luciferase
b) pMet7-HA-Tyk2(C)-p53(N)+pMG1-EFHA1+pXP2d2-rPAPI-luciferase
c) pMet7-HA-Tyk2(C)-p53(N)+pMG2-MDM2+pXP2d2-rPAPI-luciferase After transfection, cells were treated with 0-14-41-123-370-1111-3333 nM Nutlin-3, final concentration. The results shown in FIG. 4 show a dose-dependent decrease of the signal for the interaction between p53 (N-terminal region containing the MDM2 binding domain) and MDM2 upon treatment with Nutlin-3, whereas the signal corresponding to the interaction with EFHA1 (which binds to Tyk2(C) itself) is unaffected by this treatment. The signal from a control transfection combining pMet7-HA-Tyk2(C)-p53(N) and the pMG1 plasmid encoding an unfused gp130 receptor fragment is low and also unaffected by Nutlin-3 treatment. These data indicate that the method can detect dynamic changes in protein complexes dependent on addition of exogenous components.

Example 4: Incorporation of Other Kinase Domains in the Method

To support the fact that the method is not limited to the use of the kinase domain derived from Tyk2, we tested fusion proteins comprising the kinase domains of Jak2 or c-Src. Similarly to Tyk2, Jak2 belongs to the Jak family of receptor-associated tyrosine kinases. c-Src belongs to the Src non-receptor tyrosine kinase family. Cells were transfected with the following combinations of plasmids (250 ng of the kinase fusion construct, 1000 ng of the gp130 fusion construct and 50 ng of the luciferase reporter construct) according to the methods described above:
a) pMet7-HA-Tyk2(C)-RTp66+pMG2-RTp66+pXP2d2-rPAPI-luciferase
b) pMet7-HA-Jak2(C)-RTp66+pMG2-RTp66+pXP2d2-rPAPI-luciferase
c) pMet7-HA-c-Src(K)-RTp66+pMG2-RTp66+pXP2d2-rPAPI-luciferase Luciferase activity is shown as fold induction relative to the luciferase activity measured in cells transfected with the same RTp66-kinase domain fusion, an unfused gp130 fragment and the luciferase reporter plasmid (pMet7-HA-Tyk2(C)-RTp66+pMG1+pXP2d2-rPAPI-luciferase in a); pMet7-HA-Jak2(C)-RTp66+pMG1+pXP2d2-rPAPI-luciferase in b); pMet7-HA-c-Src(K)-RTp66+pMG1+pXP2d2-rPAPI-luciferase in c)). The fold induction for each tested interaction was calculated as the ratio of the luciferase activity measured relative to the luciferase activity measured for the corresponding background signal. The result (FIG. 5) indicates that the interaction between RTp66 subunits can also be detected using fusion proteins with kinase domains of other kinases than that of Tyk2.

Example 5: Inducible Version of the Method

Figure 5:
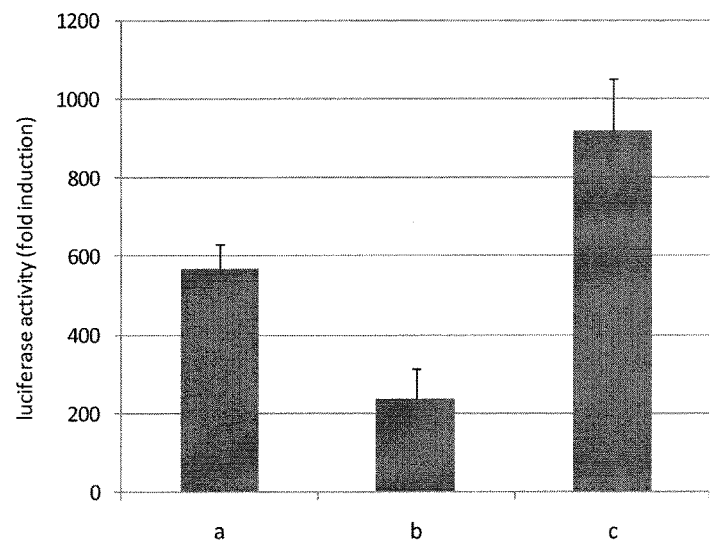
FIG. 5: Detection of the interaction between HIV1 Reverse Transcriptase (RT) p66 subunits in assay variants that comprise mutant Jak2 or c-Src kinase fusion proteins. Cells were transfected with the following plasmids: a) pMet7-HA-Tyk2(C)-RTp66+pMG2-RTp66+pXP2d2-rPAPI-luciferase; b) pMet7-HA-Jak2(C)-RTp66+pMG2-RTp66+pXP2d2-rPAPI-luciferase; and c) pMet7-HA-c-Src(K)-RTp66+pMG2-RTp66+pXP2d2-rPAPI-luciferase. Luciferase activity is shown as fold induction relative to the luciferase activity measured in cells transfected with the same RTp66-kinase fusion, an unfused gp130 fragment and the luciferase reporter plasmid (pMet7-HA-Tyk2(C)-RTp66+pMG1+pXP2d2-rPAPI-luciferase in a); pMet7-HA-Jak2(C)-RTp66+pMG1+pXP2d2-rPAPI-luciferase in b); pMet7-HA-c-Src(K)-RTp66+pMG1+pXP2d2-rPAPI-luciferase in c)). Error bars indicate standard deviation.
Figure 6:
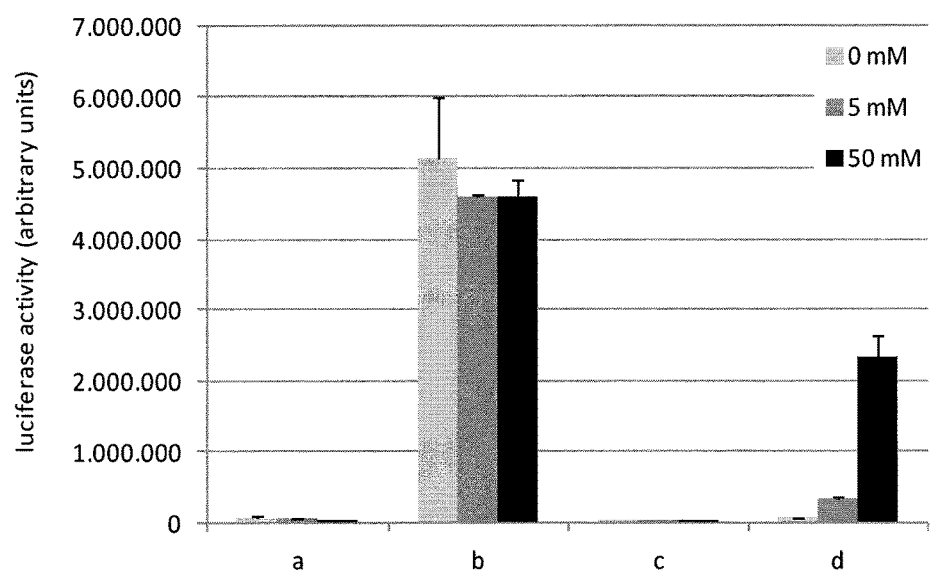
FIG. 6: Detection of the interaction between HIV1 Reverse Transcriptase (RT) subunits in an inducible assay variant. Cells were transfected with the following plasmids: a) pMet7-HA-Tyk2(C)-RTp66+pMG1+pXP2d2-rPAPI-luciferase; b) pMet7-HA-Tyk2(C)-RTp66+pMG2-RTp51+pXP2d2-rPAPI-luciferase; c) pMet7-HA-Tyk2(R1027A)-RTp66+pMG1+pXP2d2-rPAPI-luciferase; and d) pMet7-HA-Tyk2(R1027A)-RTp66+pMG2-RTp51+pXP2d2-rPAPI-luciferase. After transfection, cells were treated with 0-5-50 mM imidazole, final concentration. Error bars indicate standard deviation.

An inducible version of the method was devised to add an additional level of control and to allow temporal separation of the protein interaction and signal generation events. The latter might be important in cases where modification of the interaction polypeptides by the kinase activity prohibits interaction. A mutant Src tyrosine kinase has been described, the activity of which is made inducible by the small molecule imidazole by an arginine to alanine mutation in the catalytic center of the enzyme (Qiao et al., 2006). The corresponding point mutation of this conserved catalytic arginine (R1027) was generated in Tyk2, fused to RTp66 and tested in an imidazole-inducible version of the assay. Cells were transfected with the following combinations of plasmids (250 ng of the kinase fusion construct, 250 ng of the gp130 fusion construct and 50 ng of the luciferase reporter construct) according to the methods described above:
a) pMet7-HA-Tyk2(C)-RTp66+pMG1+pXP2d2-rPAPI-luciferase
b) pMet7-HA-Tyk2(C)-RTp66+pMG2-RTp51+pXP2d2-rPAPI-luciferase
c) pMet7-HA-Tyk2(R1027A)-RTp66+pMG1+pXP2d2-rPAPI-luciferase
d) pMet7-HA-Tyk2(R1027A)-RTp66+pMG2-RTp51+pXP2d2-rPAPI-luciferase After transfection, cells were treated with 0.5-50 mM imidazole, final concentration. The results are represented in FIG. 5, showing an imidazole-inducible signal specifically in cells expressing a fusion containing the Tyk2 arginine to alanine mutation. Maximal imidazole-dependent induction of the signal, indicative of the interaction between HIV RTp66 and RTp51, was compared 36-fold to untreated cells. Cells transfected with the Tyk2(C) fusion described earlier did not exhibit any imidazole regulation. Background signal observed in cells transfected with combinations of the Tyk2 fusion construct and a plasmid encoding an unfused gp130 fragment (pMG1) similarly was unaffected by imidazole treatment. These results indicate that it is possible to control the interaction assay by applying a chemically inducible kinase.

REFERENCES

Adachi A., H. E. Gendelman, S. Koenig, T. Folks, R. Willey, A. Rabson, and M. A. Martin (1986). Production of acquired immunodeficiency syndrome-associated retrovirus in human and nonhuman cells transfected with an infectious molecular clone. *J. Virol.* 59:284-291.

Caligiuri M., L. Molz, Q. Liu, F. Kaplan, J. P. Xu, J. Z. Majeti, R. Ramos-Kelsey, K. Murthi, S. Lievens, J. Tavernier, and N. Kley (2006). MASPIT: three-hybrid trap for quantitative fingerprinting of small molecule-protein interactions in mammalian cells. *Chem. Biol.* 13:711-722.

Eyckerman S., A. Verhee, J. Van der Heyden, I. Lemmens, X. Van Ostade, J. Vandekerckhove, and J. Tavernier (2001). Design and application of a cytokine-receptor-based interaction trap. *Nature Cell Biology* 3:1114-1119.

Fields S. and O. K. Song (1989). A novel genetic system to detect protein-protein interactions. *Nature* 340:245-246.

Lamesch P., N. Li, S. Milstein, C. Fan, T. Hao, G. Szabo, Z. Hu, K. Venkatesan, G. Bethel, P. Martin, P., et al. (2007). hORFeome v3.1: a resource of human open reading frames representing over 10,000 human genes. *Genomics* 89:307-315.

Lemmens I., S. Eyckerman, L. Zabeau, D. Catteeuw, E. Vertenten, K. Verschueren, D. Huylebroeck, J. Vandekerckhove, and J. Tavernier (2003). Heteromeric MAPPIT: a novel strategy to study modification-dependent protein-protein interactions in mammalian cells. *Nucleic Acids Research* 31.

Lievens S., N. Vanderroost, J. Van der Heyden, V. Gesellchen, M. Vidal, and J. Tavernier (2009). Array MAPPIT: high-throughput interactome analysis in mammalian cells. *J. Proteome Res.* 8:877-886.

Pattyn E., D. Lavens, J. Van der Heyden, A. Verhee, S. Lievens, I. Lemmens, S. Hallenberger, D. Jochmans, and J. Tavernier (2008). MAPPIT (MAmmalian Protein-Protein Interaction Trap) as a tool to study HIV reverse transcriptase dimerization in intact human cells. *Journal of Virological Methods* 153:7-15.

Qiao Y., H. Molina, A. Pandey, J. Zhang, and P. A. Cole (2006). Chemical rescue of a mutant enzyme in living cells. *Science* 311:1293-1297.

Silvennoinen O., B. A. Witthuhn, F. W. Quelle, J. L. Cleveland, T. Yi, and J. N. Ihle (1993). Structure of the murine Jak2 protein-tyrosine kinase and its role in interleukin 3 signal transduction. *Proc. Natl. Acad. Sci. U.S.A.* 90:8429-8433.

Takebe Y., M. Seiki, J. Fujisawa, P. Hoy, K. Yokota, K. Arai, M. Yoshida, and N. Arai (1988). SR alpha promoter: an efficient and versatile mammalian cDNA expression system composed of the simian virus 40 early promoter and the R-U5 segment of human T-cell leukemia virus type 1 long terminal repeat. *Mol. Cell. Biol.* 8:466-472.

Vassilev L. T., B. T. Vu, B. Graves, D. Carvajal, F. Podlaski, Z. Filipovic, N. Kong, U. Kammlott, C. Lukacs, C. Klein, et al. (2004). In vivo activation of the p53 pathway by small-molecule antagonists of MDM2. *Science* 303:844-848.

Venezia C. F., K. J. Howard, M. E. Ignatov, L. A. Holladay, and M. D. Barkley (2006). Effects of efavirenz binding on the subunit equilibria of HIV-1 reverse transcriptase. *Biochemistry* 45:2779-2789.

---

The invention claimed is:

1. A cytoplasmic protein complex comprising:
a first recombinant fusion protein comprising a monomeric mutant tyrosine kinase fused to a first interaction polypeptide, wherein the monomeric mutant tyrosine kinase is continuously in the active state;
a second recombinant fusion protein comprising a domain fused to a second interaction polypeptide, wherein the domain comprises a reporter phosphorylation site distinct from any phosphorylation site in the monomeric mutant tyrosine kinase;
wherein the cytoplasmic protein complex is assembled by interaction between the first and second interaction polypeptides;
wherein the cytoplasmic protein complex is phosphorylatable at the reporter phosphorylation site by the monomeric mutant tyrosine kinase in the cytoplasmic protein complex; and
wherein the monomeric mutant tyrosine kinase comprises a sequence of at least 95% identity to SEQ ID NO: 1 and wherein said sequence has tyrosine kinase activity.

2. The cytoplasmic protein complex according to claim 1, wherein the first and second interaction polypeptides are not identical.

3. The cytoplasmic protein complex according to claim 1, wherein the monomeric mutant tyrosine kinase comprises a V678F mutation.

4. A cytoplasmic protein complex comprising:
a first recombinant fusion protein comprising a monomeric mutant tyrosine kinase fused to a first interaction polypeptide, wherein the monomeric mutant tyrosine kinase is continuously in the active state or is inactive and activated by addition of an exogenous small compound;
a second recombinant fusion protein comprising a domain fused to a second interaction polypeptide, wherein the domain comprises a reporter phosphorylation site distinct from any phosphorylation site in the monomeric mutant tyrosine kinase;
wherein the cytoplasmic protein complex is assembled by interaction between the first and second interaction polypeptides;
wherein the cytoplasmic protein complex is phosphorylatable at the reporter phosphorylation site by the monomeric mutant tyrosine kinase in the cytoplasmic protein complex; and
wherein the first recombinant fusion protein comprises SEQ ID NO: 1.

5. The cytoplasmic protein complex according to claim 1, wherein the second recombinant fusion protein comprises SEQ ID NO:3.

6. A method of using the cytoplasmic protein complex of claim 1 to detect a compound-compound interaction, the method comprising:

expressing both the first recombinant and second recombinant fusion proteins of the cytoplasmic protein complex in a cell; and
identifying and/or selecting those cells in which the reporter phosphorylation site is phosphorylated.

7. The method according to claim 6, wherein the cell is a eukaryotic cell.

8. The method according to claim 7, wherein the eukaryotic cell is a mammalian cell.

9. The method according to claim 6, wherein the kinase comprises SEQ ID NO: 1.

10. The method according to claim 6, wherein the second recombinant fusion protein comprises SEQ ID NO:3.

11. An isolated cell comprising the cytoplasmic protein complex of claim 1.

12. The isolated cell of claim 11, wherein the cell is a eukaryotic cell.

13. The isolated cell of claim 12, wherein the eukaryotic cell is a mammalian cell.

14. A method of using the isolated cell of claim 11 for detecting a compound that disrupts a polypeptide-polypeptide interaction, the method comprising:
growing the isolated cell, wherein the cytoplasmic protein complex thereof comprises the polypeptide-polypeptide interaction to be disrupted, in the absence of and in the presence of at least one compound;
comparing the phosphorylation of the reporter phosphorylation site in the second recombinant fusion protein of the cytoplasmic protein complex of cells, grown in the presence of and in the absence of the at least one compound; and
identifying and/or selecting cells wherein the reporter phosphorylation site is not phosphorylated.

15. The cytoplasmic protein complex of claim 1, wherein the reporter phosphorylation site is part of a Signal Transducer and Activator of Transcription (STAT) binding site.

16. The cytoplasmic protein complex of claim 1, wherein the monomeric mutant tyrosine kinase is a Tyk2 mutant.

17. A cytoplasmic protein complex comprising:
a first recombinant fusion protein comprising a monomeric mutant Tyk2 kinase fused to a first interaction polypeptide;
a second recombinant fusion protein comprising a gp130 domain comprising at least one phosphorylation site that can be phosphorylated by the monomeric mutant Tyk2 kinase, wherein the gp130 domain is fused to a second interaction polypeptide;
wherein the first interaction polypeptide is bound to the second interaction polypeptide; and
wherein a wild-type form of the mutant Tyk2 kinase can phosphorylate a wild-type gp130 domain comprising the phosphorylation site for Tyk2.

* * * * *